US011969505B2

(12) United States Patent
Paukkonen et al.

(10) Patent No.: US 11,969,505 B2
(45) Date of Patent: Apr. 30, 2024

(54) METHOD FOR FREEZE-DRYING CELLS IN A HYDROGEL COMPRISING NANOFIBRILLAR CELLULOSE AND FREEZE-DRIED CELLS IN AN AEROGEL COMPRISING NANOFIBRILLAR CELLULOSE

(71) Applicant: UPM-KYMMENE CORPORATION, Helsinki (FI)

(72) Inventors: Heli Paukkonen, Espoo (FI); Vili-Veli Auvinen, Espoo (FI); Marjo Yliperttula, Espoo (FI); Patrick Laurén, Espoo (FI); Arto Urtti, Kuopio (FI); Timo Laaksonen, Hyvinkää (FI); Arto Merivaara, Helsinki (FI); Tiina Hakkarainen, Kaavi (FI); Outi Monni, Espoo (FI); Anne Mäkelä, Espoo (FI); Petter Somersalo, Helsinki (FI); Piia-Riitta Karhemo, Nummela (FI); Heikki Joensuu, Espoo (FI); Raili Koivuniemi, Vantaa (FI); Kari Luukko, Espoo (FI); Markus Nuopponen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 59 days.

(21) Appl. No.: 17/712,732

(22) Filed: Apr. 4, 2022

(65) Prior Publication Data
US 2022/0249378 A1 Aug. 11, 2022

Related U.S. Application Data

(62) Division of application No. 16/468,390, filed as application No. PCT/EP2017/071441 on Aug. 25, 2017, now Pat. No. 11,324,701.

(30) Foreign Application Priority Data

Dec. 15, 2016 (EP) .................... 16397537

(51) Int. Cl.
*A01N 1/02* (2006.01)
*A61K 9/06* (2006.01)
*A61K 9/19* (2006.01)
*A61K 47/10* (2017.01)
*A61K 47/26* (2006.01)
*A61K 47/38* (2006.01)
*C12N 5/00* (2006.01)
*C12N 5/09* (2010.01)
*F26B 5/06* (2006.01)

(52) U.S. Cl.
CPC .............. *A61K 9/19* (2013.01); *A01N 1/0221* (2013.01); *A01N 1/0231* (2013.01); *A61K 9/06* (2013.01); *A61K 47/10* (2013.01); *A61K 47/26* (2013.01); *A61K 47/38* (2013.01); *C12N 5/0062* (2013.01); *C12N 5/0693* (2013.01); *F26B 5/06* (2013.01); *C12N 2513/00* (2013.01); *C12N 2533/78* (2013.01)

(58) Field of Classification Search
None
See application file for complete search history.

(56) References Cited

U.S. PATENT DOCUMENTS

| | | |
|---|---|---|
| 5,962,005 A | 10/1999 | Saga et al. |
| 6,202,946 B1 | 3/2001 | Virtanen |
| 2009/0130756 A1 | 5/2009 | Klann et al. |
| 2012/0322663 A1 | 12/2012 | Harel et al. |
| 2013/0018112 A1 | 1/2013 | Thielemans et al. |
| 2013/0330417 A1* | 12/2013 | Dong ............... A61L 15/28 428/338 |
| 2015/0093560 A1 | 4/2015 | Nemoto et al. |
| 2016/0263228 A1 | 9/2016 | Kluge et al. |
| 2016/0298077 A1 | 10/2016 | Salmons et al. |
| 2016/0325008 A1 | 11/2016 | Laukkanen et al. |
| 2017/0027168 A1 | 2/2017 | Heath |
| 2019/0343889 A1 | 11/2019 | Luukko et al. |
| 2020/0078305 A1 | 3/2020 | Auvinen et al. |

FOREIGN PATENT DOCUMENTS

| | | |
|---|---|---|
| CN | 104920339 A | 9/2015 |
| CN | 105254917 A | 1/2016 |
| CN | 105363070 A | 3/2016 |
| EP | 2216345 A1 | 8/2010 |
| JP | 2015105453 A | 6/2015 |
| WO | 2010142850 A1 | 12/2010 |
| WO | 2013072563 A1 | 5/2013 |
| WO | 2016097490 A1 | 6/2016 |

OTHER PUBLICATIONS

U.S. Appl. No. 17/245,445 "A Method for Freeze-Drying a Hydrogel Composition and a Freeze-Dried Hydrogel Composition", filed Apr. 30, 2021.
Cicero, A. L., et al., "Exosomes released by keratinocytes modulate melanocyte pigmentation", Nature Communications; Published Jun. 24, 2015; 8 pages.
Hakkarainen, T. et al., "Nanofibrillar cellulose wound dressing in skin graft donor site treatment", Journal of Controlled Release, vol. 244, 2016; pp. 292-301.
International Search Report for International Application No. PCT/EP2017/071441; International Filing Date: Aug. 25, 2017; dated Aug. 11, 2017; 5 pages.

(Continued)

*Primary Examiner* — Emily A Cordas
(74) *Attorney, Agent, or Firm* — CANTOR COLBURN LLP

(57) ABSTRACT

The present disclosure provides a method for freeze-drying cells in a hydrogel comprising nanofibrillar cellulose, the method comprising providing a hydrogel comprising nanofibrillar cellulose, providing cells, combining the cells and the hydrogel comprising nanofibrillar cellulose to form a cell system, and freeze drying the cell system to obtain dried cells in a hydrogel comprising nanofibrillar cellulose. The present disclosure also provides a freeze-dried hydrogel comprising nanofibrillar cellulose and cells.

19 Claims, 7 Drawing Sheets

(56) References Cited

OTHER PUBLICATIONS

Liu, J. et al., "Hemicellulose-reinforced nanocellulose hydrogels for wound healing application", Cellulose, vol. 23, 2016; pp. 3129-3143.

Muller, A. et al., "Bacterial nanocellulose with a shape-memory effect as potential drug delivery system", RSC Advances, vol. 4, 2015; pp. 57173-57184.

Nahr, F. K. et al., "Optimization of the nanocellulose based cryoprotective medium to enhance the viability o freeze dried Lactobacillus plantarum using response surface methodology", LWT—Food Science and Technology, vol. 64, 2015; pp. 326-332.

Niu Dan, "The Encapsulation and Vitrification Preservation of a Hydrogel Comprising Human Umbilical Vein Endothelial Cell", University of Science and Technology of China. Chinese Master's Theses Full-text Database: Medicine and Health Sciences; Oct. 15, 2016; 7 pages, English translation.

Nordli, H. R. et al., "Producing ultrapure wood cellulose nanofibrils and evaluating the cytotoxicity using human skin cells", Carbohydrate Polymers, vol. 150, 2016; pp. 65-73.

Poirier, J.M., "Porous Scaffolds of Cellulose Nanofibres Bound with Crosslinked Chitosan and Gelatine for Cartilage Applications: Processing and Characterization", Master's Thesis, 2013; 52 pages.

Prestrelski et al., "Separation of Freezing-and Drying-Induced Denaturation of Lyophilized Proteins Using Stress-Specific Stabilization: II. Structural Studies Using Infrared Spectroscopy." Archives of Biochemestry and Biophysics, vol. 303, No. 2, 1993; pp. 465-473.

Valo, H. et al., "Drug release from nanoparticles embedded in four different nanofibrillar cellulose aerogels", European Journal of Pharmaceutical Sciences, vol. 50, 2013; pp. 69-77.

Valo, H., "Bipolymer-Based Nanoparticles for Drug Delivery", Academic Dissertation; Division of Pharmaceutical Technology, 2012; 58 pages.

Written Opinion of the International Searching Authority for International Application No. PCT/EP2017/071441; International Filing Date: Aug. 25, 2017; dated Aug. 11, 2017; 5 pages.

Zepic, V., "Morphological, thermal, and structural aspects of dried and redispersed nanofibrillated cellulose (NFC)", Holzforschung, vol. 68, No. 6, 2014; pp. 657-667.

Auvinen, Vili-Veli et al., "Effectes of nanofibrillated cellulose hydrogels on adipose tissue extract and hepatocellular carcinoma cell spheroids in freeze-drying", Cryobiology, vol. 91, 2019; 57 pages.

\* cited by examiner

METHOD FOR FREEZE-DRYING CELLS IN A HYDROGEL COMPRISING NANOFIBRILLAR CELLULOSE AND FREEZE-DRIED CELLS IN AN AEROGEL COMPRISING NANOFIBRILLAR CELLULOSE

CROSS-REFERENCE TO RELATED APPLICATIONS

This application is divisional application of U.S. application Ser. No. 16/468,390, filed Jun. 11, 2019, which is a National Stage application of PCT/EP2017/071441, filed Aug. 25, 2017, which claims benefit of European Application No. 16397537.8 filed on Dec. 15, 2016, each of which is incorporated by reference herein in its entirety.

TECHNICAL FIELD

The present disclosure relates to methods for freeze-drying cells, and freeze-dried cells obtained with said method. More particularly the present disclosure relates to methods for freeze-drying cells in a hydrogel comprising nanofibrillar cellulose and to freeze-dried cells in an aerogel comprising nanofibrillar cellulose

BACKGROUND

With current knowledge, freeze-drying of complex or large mammalian cells causes irreversible damage to the cell and the freeze-dried cells tend to lose their three-dimensional shape when dried. Therefore there is need to find a method which may be used for freeze-drying such cells, and which could protect the cells during freezing.

The obtained dried product should be dry, active, shelf stable, clean and sterile, ethically acceptable, pharmaceutically elegant, readily soluble and simple to reconstitute, and the process should be economically practicable.

SUMMARY

Nanofibrillar cellulose refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water.

Nanofibrillar cellulose production techniques are based on grinding of aqueous dispersion of pulp fibers. The concentration of nanofibrillar cellulose in dispersions is typically very low, usually around 0.3-5%. After the grinding or homogenization process, the obtained nanofibrillar cellulose material is a dilute viscoelastic hydrogel.

Because of its nanoscale structure nanofibrillar cellulose has unique properties which enable functionalities which cannot be provided by conventional cellulose. It was found out that cells, especially eukaryotic cells, may be grown in nanofibrillar cellulose matrix in three-dimensional culture, wherein the cells may grow as spheroids. Such cell cultures are efficient, as the cell in the 3D culture can communicate easily with each other and form tissue-like colonies. This is not possible by using conventional 2D cultures.

However, because of the nanoscale structure nanofibrillar cellulose is also a challenging material. For example dewatering or handling of nanofibrillar cellulose may be difficult. Further, after dewatering it is generally difficult to rehydrate or regel the dried material to obtain material having equal properties to the original nanofibrillar cellulose before the dewatering or drying. Especially challenging dewatering process is freeze-drying.

In the present application it is disclosed how to use the nanofibrillar cellulose hydrogel as a lyoprotective matrix for freeze-drying cells, such as mammalian cells. It has been a problem how nanofibrillar cellulose (NFC) hydrogel as such can be freeze-dried and then rehydrated with no loss in rheological or diffusive properties. For example, the drying of NFC promotes irreversible hydrogen bonding between neighboring NFC nanofibers, known as hornification. However, when cells were freeze-dried in nanofibrillar cellulose hydrogel, the hydrogel itself was found to provide lyoprotective properties. When 2D cultures, even with trehalose, were lyophilized, the cells did not survive. It was also found out that specific auxiliary agents may to be used to further protect the hydrogels and the cells during freezing and lyophilization.

One embodiment provides a method for freeze-drying cells in a hydrogel comprising nanofibrillar cellulose, the method comprising
 providing a hydrogel comprising nanofibrillar cellulose,
 providing cells,
 combining the cells and the hydrogel comprising nanofibrillar cellulose to form a cell system, and
 freeze drying the cell system to obtain dried cells in an aerogel comprising nanofibrillar cellulose.

One embodiment provides a method for freeze-drying extracellular vesicles in a hydrogel comprising nanofibrillar cellulose, the method comprising
 providing a hydrogel comprising nanofibrillar cellulose,
 providing extracellular vesicles,
 combining the vesicles and the hydrogel comprising nanofibrillar cellulose to form a vesicle system, and
 freeze drying the vesicle system to obtain dried extracellular vesicles in an aerogel comprising nanofibrillar cellulose.

The methods may comprise providing one or more cryoprotective and/or lyoprotective agent(s) and adding the one or more cryoprotective and/or lyoprotective agent(s) to the cell system or to the vesicle system.

One embodiment provides a freeze-dried aerogel comprising nanofibrillar cellulose, cells and optionally one or more cryoprotective and/or lyoprotective agent(s), wherein the moisture content of the freeze-dried aerogel is 10% or less, preferably in the range of 1-10% (w/w), such as 2-8% (w/w).

One embodiment provides a freeze-dried aerogel comprising nanofibrillar cellulose and extracellular vesicles, wherein the moisture content of the freeze-dried aerogel is 10% or less, preferably in the range of 1-10% (w/w), such as 2-8% (w/w).

The main embodiments are characterized in the independent claims. Various embodiments are disclosed in the dependent claims. The embodiments recited in claims and in the embodiments are mutually freely combinable unless otherwise explicitly stated.

It was surprisingly found out that nanofibrillar cellulose hydrogel could act as a lyoprotective matrix in a freeze-drying process. In the process ingredients may be included in the hydrogel. The ingredients may include cells, such as eukaryotic or prokaryotic cells, especially mammalian cells, but also other agents, such as cryo- and/or lyoprotective agents, pharmaceutical or therapeutical agents, nutrients, other chemical agents, active agents or other large or small molecules. However, it was specifically found out that the nanofibrillar cellulose hydrogel as such provided efficient lyoprotective properties for cells. This is advantageous because especially eukaryotic cells, more particularly mammalian cells, are challenging to freeze-dry. One reason for this could be the mitochondria or vesicles present in the cells, which are easily damaged during the process.

It was possible to obtain a dried product, which could be rehydrated or redispersed into a form which restores the original properties of the hydrogel comprising nanofibrillar cellulose, i.e. the dried product can be regelled. Such properties include for example cell properties, gel properties and controlled release of active compounds or pharmaceutical ingredients.

Nanofibrillar cellulose was discovered to act as a lyoprotective matrix that can withstand freezing and drying without mechanical rupture. Nanofibrillar cellulose may also act as a cryoprotective matrix. It is inert, clean of contaminants, holds enough liquid to achieve high porosity and can be shaped as well-defined geometrical units. Further, the nanofibrillar cellulose is able to release absorbed active products when flooded with rehydration liquid. To release cell, usually also enzyme addition is required to degrade the gel.

It was discovered that the cells retained their original morphology and no ruptures or collapsing was detected. Further, the rehydrated cells attached to the surface of the culture flask, which indicates the viability of the cells. The lyoprotective effects of the nanofibrillar cellulose hydrogel were demonstrated in tests.

Further, it was discovered that extracellular vesicles, such as microvesicles, could survive the freeze-drying of the cells when the method described herein was used. As microvesicles have a role in intercellular messaging, the preservation of microvesicles during the freeze-drying enhances the ability of the cell culture to start growing efficiently as a 3D colony immediately after rehydration. It is possible to freeze-dry also separate microvesicles with the method.

The nanofibrillar cellulose hydrogel provides a hydrophilic matrix, which is non-toxic, biocompatible and also biodegradable. For example the matrix can be degraded enzymatically, for example by adding cellulase. On the other hand the hydrogel is stable at physiological conditions. Cells, especially challenging eukaryotic cells, such as mammalian cells, can be cultured in nanofibrillar cellulose hydrogel in three-dimensional cultures, freeze-dried, and rehydrated to restore the 3D culture.

The feature that the hydrogel can be enzymatically digested, is advantageous especially is the case of cells. When a cell system is dried, its biological clock stops; similarly, when frozen. Therefore, a completely new generation of "just-add-water" cell products may be provided, where the supportive dry NFC matrix could be removed after transportation. This may in return accelerate the cell research, as the research typically requires a lot of currently irreplaceable handwork. Also, transporting and storing dried ready-to-use cell systems would be more affordable, as complex cooling systems would not be required. For example 3D cultivated cell spheroid products could be made directly accessible to researchers without the requirement to seed and grow them first. As 3D spheroids better mimic real tumors, particularly for example if hypoxia is considered, their usage will likely increase in the near future. Later, clinical applications for the freeze-dried cell products could be considered in a more serious manner.

Further, the presence of the selected cryo- and/or lyoprotectants had no effect to the release profile of the agents from the gels. By drying the hydrogel it is possible to obtain a very long shelf life for medical or scientific products. Especially gels containing cells or active agents, which are unstable at moist conditions, such as proteins, DNA/RNA, and other agents sensitive to hydrolysis, can be successfully freeze-dried into forms containing little or practically no water and therefore having a prolonged stability and shelf life. Such freeze-dried products may be stored even at room temperature and may be regelled prior to use by adding liquid, such as water, diluted saline or diluted cell culture medium.

Certain advantageous properties of the hydrogel comprising nanofibrillar cellulose include flexibility, elasticity and remouldability. As the hydrogel contains a lot of water, it may also show good permeability. The hydrogels of the embodiments also provide high water retention capacity and molecule diffusion property speed The hydrogels described herein are useful in medical and scientific applications, wherein the materials comprising nanofibrillar cellulose are in contact with living matter. The products containing nanofibrillar cellulose as described herein are highly biocompatible with the living matter and provide several advantageous effects. Without binding to any specific theory, it is believed that a hydrogel comprising very hydrophilic nanofibrillar cellulose having a very high specific surface area, and thus high water retention ability, when applied against cells or tissue, provides favourable moist environment between the cells or tissue and the hydrogel comprising nanofibrillar cellulose. The high amount of free hydroxyl groups in the nanofibrillar cellulose forms hydrogen bonds between the nanofibrillar cellulose and water molecules and enables gel formation and the high water retention ability of the nanofibrillar cellulose. Because of the high amount of water in the nanofibrillar cellulose hydrogel, only water is supposed to be in contact with cells or tissue, and which also enables migration of fluids and/or agents.

BRIEF DESCRIPTION OF THE DRAWINGS

The embodiments will be explained in the following with reference to the appended drawings, where.

DETAILED DESCRIPTION

Figure 1:
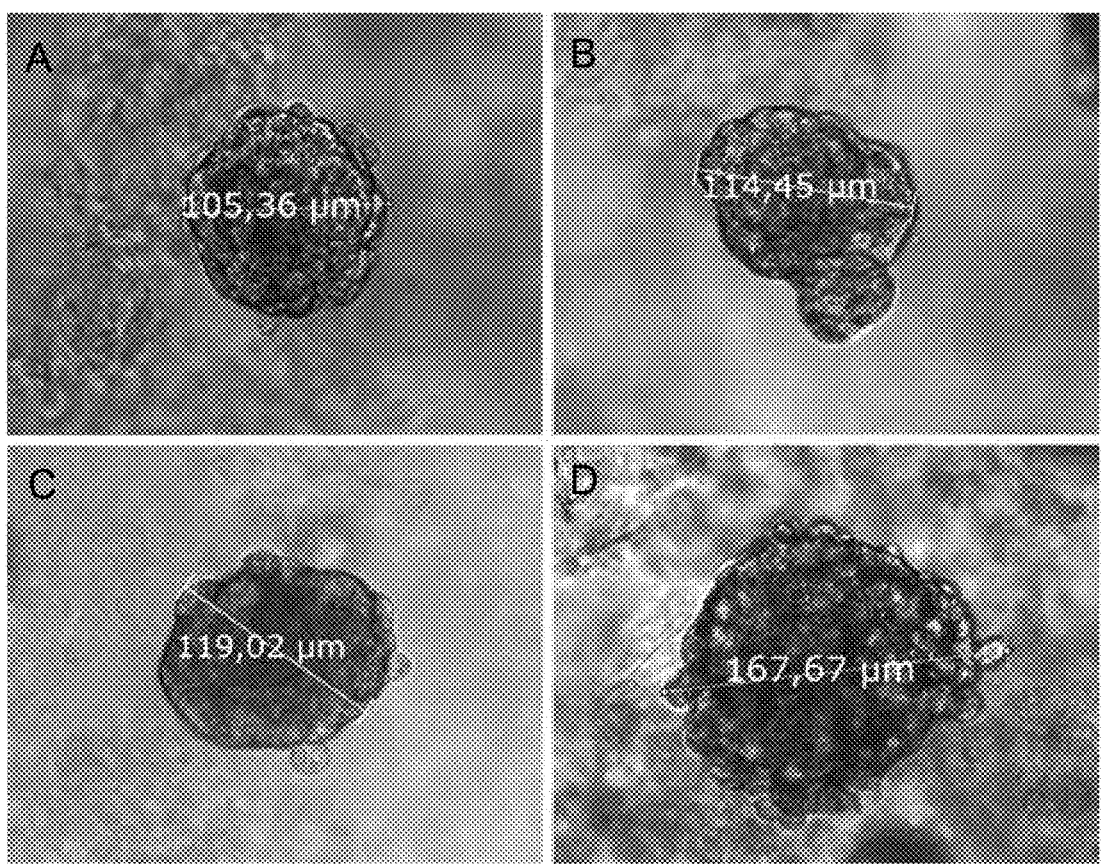
FIG. 1 shows day 5 Hep G2 cell spheroids cultivated in 0.8% GrowDex® hydrogel imaged after 24 hours of trehalose incubation prior to freezing phase. Images (A), (B) and (C) display typical spheroids with a diameter between 100 and 120 µm. (D) shows a larger spheroid with a diameter over 160 µm.

Freeze-drying, also known as lyophilization, is a physical process, where water is removed controllably from a frozen substance by sublimation. It is a sensitive drying method when compared to other drying methods, such as oven drying and spray drying, and therefore especially suitable for drying proteins and other biological compounds.

Freeze-drying is a multistage operation, in which the success of each step is critical for the outcome. In freeze-drying an active substance is dried that needs to keep its prime properties, such as the correct 3D structure in the case of proteins. The process includes a surrounding "medium" which refers to the added bulking agents, such as cryo- and lyoprotectors, stabilizers, emulsifiers and antioxidants. The process in general comprises seven phases, of which in the first one the substance is prepared by adding the required bulking agents. Next, in the second phase, the substance is frozen close to its Tg' point (lower transition temperature), which is unique to each mixture. Then in the third step, the substance is dried for an extended period of time in a vacuum and any frozen water is removed through sublimation. This phase is known as the primary drying phase, or sublimation phase. Under normal conditions, the drying would happen as a phase transition from liquid to gas phase. However, in freeze-drying the temperature is decreased until the substance is frozen, and then the pressure is decreased in the sublimation step. A process of shifting takes place through the solid phase around the triple point of water.

Next, in the fourth phase of freeze-drying, any non-frozen bound water is extracted by increasing the temperature while decreasing the pressure. This step is known as the secondary drying or desorption phase. When the substance is dry, it has to be removed from the freeze-drying machinery in the fifth step; conditioning and storage. In this phase, the substance easily gets damaged by water, light, oxygen and contaminants. In the sixth step of freeze-drying, the samples are placed in the ultimate storage. The required storage parameters should be optimized for each substance individually. Lastly, at the seventh, reconstitution phase, the sample is rehydrated in order to recreate the original system for use. If the developed freeze-drying cycle is successful, the rehydrated substance should carry the same or nearly the same properties as the original substance.

The present application discloses the use of nanofibrillar cellulose hydrogel as a lyoprotective matrix in freeze-drying process. Nanofibrillar cellulose matrix was found to be advantageous when freeze-drying cells, especially eukaryotic cells, such as mammalian cells. Naturally all kinds of cells may be freeze-dried using the methods disclosed herein, such as prokaryotic cells, as well as extracellular vesicles, such as microvesicles. Cryoprotectants and/or lyoprotectants may be used in the process.

It was found out that the nanofibrillar cellulose used as a matrix acted as a lyoprotectant, which effect could be enhanced by using other cryo- or lyoprotective agents, as disclosed herein. Therefore a synergistic effect of enhanced cryo- and lyoprotection was obtained.

The present disclosure provides hydrogels comprising nanofibrillar cellulose, which may be also called as nanofibrillar cellulose hydrogels. The hydrogels may be provided as products, which may contain also other substances or other elements, such as reinforcing materials, covering materials, active agents, salts or the like. The hydrogels may be also provided or called as medical hydrogels or medical products.

The present application provides a method for freeze-drying cells in a hydrogel comprising nanofibrillar cellulose, the method comprising providing a hydrogel comprising nanofibrillar cellulose,
providing cells,
combining the cells and the hydrogel comprising nanofibrillar cellulose to form a cell system. The cells may be provided in aqueous medium, such as cell culture medium. Aqueous medium may also be added to the cell system. When extracellular vesicles are concerned, the formed system may be called as a vesicle system or extracellular vesicle system. The procedure with the vesicles is otherwise similar to the procedure with cells, and similar products are obtained, only with vesicles instead of cells. The method and the obtained product may also include both the cells and the vesicles.

In one embodiment the method comprises culturing the cells in the cell system. In such case a cell culture is formed. In many cases the cell system may be also called as cell culture.

Initially the cells may be pre-cultured in a separate culture, and recovered and transferred into a new medium, which may be similar or different than the culture medium. A cell suspension is obtained. This, or another cell suspension, may be combined and/or mixed with the nanofibrillar cellulose, such as a hydrogel comprising nanofibrillar cellulose, to obtain or form a cell system. If cells are cultured in the cell system a cell culture is formed. The cell culture may be 2D culture or a 3D culture. In one embodiment the cell culture is a 3D cell culture. The cells may be cultured or incubated for a period of time. In one embodiment the method comprises providing one or more cryoprotective and/or lyoprotective agent(s), for example in a culture medium, and adding the one or more cryoprotective and/or lyoprotective agent(s) to the cell system or to the cell culture. For example the cell culture medium may be changed into medium containing one or more cryoprotective and/or lyoprotective agent(s). Alternatively, or in addition, the one or more cryoprotective and/or lyoprotective agent(s) may be added to the cell culture medium in the cell culture. In one example trehalose is included in the culture medium first and the cells are incubated with trehalose for a period of time, for example for about 12-24 hours, for example with 20-100 mM trehalose medium, before any other cryoprotective and/or lyoprotective agent(s) is/are added. Finally the method comprises freeze drying the cell culture to obtain dried cells in a hydrogel comprising nanofibrillar cellulose.

One embodiment provides a hydrogel comprising nanofibrillar cellulose and one or more cryoprotective and/or lyoprotective agent(s). Such a hydrogel may be provided for combining with the cells as described in previous.

The cells may be prokaryotic cells, such as bacterial cells, or they may be eukaryotic cells. Eukaryotic cells may be plant cells, yeast cells or animal cells. Examples of eukaryotic cells include transplantable cells, such as stem cells, for example omnipotent, pluripotent, multipotent, oligopotent or unipotent cells. In case of human embryonic stem cells the cells may be from a deposited cell line or made from unfertilized eggs, i.e. "parthenote" eggs or from parthenogenetically activated ovum, so that no human embryos are destroyed. The cells may be cultured in the hydrogel, and they may be also freeze-dried in it. The cells can be maintained and proliferated on or in the hydrogel without animal or human based chemicals originating outside the cells. The cells may be evenly dispersed on or in the hydrogel.

Examples of cells include stem cells, undifferentiated cells, precursor cells, as well as fully differentiated cells and combinations thereof. In some examples the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. The cells may be tumor or cancer cells, genetically modified cells, such as transgenic cells, cisgenic cells or knock-out cells, or pathogenic cells. Such cells may be used for example for drug research.

In one embodiment the cells are eukaryotic cells, such as mammalian cells. Examples of mammalian cells include human cells, mouse cells, rat cells, rabbit cells, monkey cells, pig cells, bovine cells, chicken cells and the like. It is to be noted that even though the advantages of the present method are best demonstrated for freeze-drying mammalian cells, the method may be also used for freeze-drying other cells, such as non-mammalian eukaryotic cells, yeast cells, or prokaryotic cells.

When cells are grown in 3D culture in nanofibrillar cellulose hydrogels, the cells grow as spheroids and may communicate with each other. Such a cell colony may be considered as a tissue. According to one definition a tissue is an ensemble of similar cells from the same origin that together carry out a specific function. Therefore the present method may be also applied for freeze-drying tissue. It is possible to provide a freeze-dried product comprising a desired cell type, which may be used instead of a real tissue for scientific research, for example for drug testing. A freeze-dried 3D cell culture or tissue culture obtained with the method disclosed herein is able to continue growth shortly after rehydration.

A freeze-dried hydrogel may be called as an aerogel, more particularly a freeze-dried aerogel. According to one definition, an aerogel is a porous ultralight material derived from a gel, in which the liquid component of the gel has been replaced with a gas. Despite their name, aerogels are solid, rigid, and dry materials that do not resemble a gel in their physical properties: the name comes from the fact that they are made from gels.

As the freeze-drying method was found to preserve extracellular vesicles, such as exosomes or microvesicles, it is possible to freeze-dry extracellular vesicles with the method to obtain dried extracellular vesicles in a hydrogel comprising nanofibrillar cellulose. Such extracellular vesicles, especially microvesicles, may be used in a method for targeting therapeutical agent(s) to target cells.

Exosomes are cell-derived vesicles that are present in most eukaryotic fluids, including blood, urine, and cultured medium of cell cultures. The diameter of exosomes may be in the range of 30-100 nm. Exosomes may be released from the cell when multivesicular bodies fuse with the plasma membrane or they are released directly from the plasma membrane. Exosomes contain various molecular constituents of their cell of origin, including proteins, RNA, lipids and metabolites. Although the exosomal protein composition varies with the cell and tissue of origin, most exosomes contain an evolutionarily-conserved common set of protein molecules. The protein content of a single exosome, given certain assumptions of protein size and configuration, and packing parameters, can be about 20 000 molecules. Exosomes can transfer molecules from one cell to another via membrane vesicle trafficking, thereby influencing the immune system, such as dendritic cells and B cells, and may play a functional role in mediating adaptive immune responses to pathogens and tumors.

Exosomes may be used as highly effective drug carriers. Composed of cellular membranes with multiple adhesive proteins on their surface, exosomes are known to specialize in cell-cell communications and provide an exclusive approach for the delivery of various therapeutic agents to target cells, such as anti-cancer drugs.

Microvesicles are one type of extracellular vesicles. They are circular fragments of plasma membrane having a diameter in the range of 100-1000 nm. Microvesicles play a role in intercellular communication and can transport mRNA, miRNA, and proteins between cells. Microvesicles act in the process of a remarkable anti-tumor reversal effect in cancer, tumor immune suppression, metastasis, tumor-stroma interactions and angiogenesis along with having a primary role in tissue regeneration. Microvesicles reflect the antigenic content of the cells from which they originate. Different cells can release microvesicles from the plasma membrane, such as megakaryocytes, blood platelets, monocytes, neutrophils, tumor cells and placenta.

A dried hydrogel comprising nanofibrillar cellulose, cells and optionally one or more cryoprotective and/or lyoprotective agent(s) is formed in the method. The hydrogel used or formed in the method may be a medical hydrogel.

The term "medical" refers to a product or use wherein the product, i.e. a product comprising the hydrogel of the embodiments, is used or is suitable for medical purposes or for scientific purposes, for example for research. A medical product may be sterilized, or it is serializable, for example by using temperature, pressure, moisture, chemicals, radiation or a combination thereof. The product, preferably the hydrogel without cells, may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. A medical product is preferably non-toxic to the target. Also UV sterilization may be used.

The nanofibrillar cellulose (NFC) hydrogel of the embodiments, such as anionic NFC hydrogel, is able to controllably release active agents, such as agents secreted by the cells, or therapeutic agents, for example pharmaceutical ingredients, as a function of time, especially when the temperature and pH are constant. It was found out that NFC hydrogel can be freeze-dried with the specific excipients and still be re-gelled. Anionic hydrogels are preferred for many applications. For example anionically modified nanofibrillar cellulose does not precipitate easily unlike the other grades. The aniconic grade is also especially suitable for releasing certain active agents.

In the tests a commercial product manufactured by UPM-Kymmene Oyj called GrowDex® was used. GrowDex® is a sterile nanofibrillated cellulose hydrogel product manufactured from birch pulp. The native GrowDex® hydrogel is highly viscous, but its viscosity can be adjusted to required conditions by throughout mixing with water-based liquids, such as cell media. If the fiber concentration is adjusted below 1.6%, the hydrogel can be dispensed by pipetting while it maintains relevantly high water retention. The hydrogel tolerates salts, changes in temperature and pH and retains its properties at least in the pH range of 6-8. However, magnesium and calcium can crosslink NFC fibers and should therefore be avoided in cell media and other additives for unwanted crosslinking. The ultrastructure of the NFC hydrogel resembles extracellular matrix (ECM). GrowDex® hydrogel is non-autofluorescent, and therefore compatible with cell staining and imagining. In case of stains that adhere to NFC fibers, the GrowDex® hydrogel structure can be enzymatically dissembled by addition of cellulase enzyme prior imagining.

In this specification, percentage values, unless specifically indicated otherwise, are based on weight (w/w). If any numerical ranges are provided, the ranges include also the upper and lower values.

Nanofibrillar Cellulose

The nanofibrillar cellulose is prepared generally from cellulose raw material of plant origin. The raw material may be based on any plant material that contains cellulose. The raw material may also be derived from certain bacterial fermentation processes. The nanofibrillar cellulose is preferably made of plant material. In one example the fibrils are obtained from non-parenchymal plant material. In such case the fibrils may be obtained from secondary cell walls. One abundant source of such cellulose fibrils is wood fibres. The nanofibrillar cellulose is manufactured by homogenizing wood-derived fibrous raw material, which may be chemical pulp. Cellulose fibers are disintegrated to produce fibrils which have the diameter of only some nanometers, which is 50 nm at the most, for example in the range of 1-50 μm, and gives a dispersion of fibrils in water. The fibrils may be reduced to size where the diameter of most of the fibrils is in the range of only 2-20 nm. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

In one embodiment the plant material is wood. Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp. In one embodiment said wood pulp is chemical pulp.

As used herein, the term "nanofibrillar cellulose" refers to cellulose fibrils or fibril bundles separated from cellulose-based fiber raw material. These fibrils are characterized by a high aspect ratio (length/diameter): their length may exceed 1 μm, whereas the diameter typically remains smaller than 200 nm. The smallest fibrils are in the scale of so-called elementary fibrils, the diameter being typically in the range of 2-12 nm. The dimensions and size distribution of the fibrils depend on the refining method and efficiency. Nanofibrillar cellulose may be characterized as a cellulose-based material, in which the median length of particles (fibrils or fibril bundles) is not greater than 50 μm, for example in the range of 1-50 μm, and the particle diameter is smaller than 1 μm, suitably in the range of 2-500 nm. In case of native nanofibrillar cellulose, in one embodiment the average diameter of a fibril is in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose may also contain small amounts of other wood components, such as hemicellulose or lignin. The amount is dependent on the plant source. Often used parallel names for nanofibrillar cellulose include nanofibrillated cellulose (NFC) and nanocellulose.

In general cellulose nanomaterials may be divided into categories according to TAPPI W13021, which provides standard terms for cellulose nanomaterials. Two main categories are "Nano objects" and "Nano structured materials". Nanostructured materials include "Cellulose microcrystals" (sometimes called as CMC) having a width of 10-12 μm and L/D <2, and "Cellulose microfibrils" having a width of 10-100 nm and a length of 0.5-50 μm. Nano objects include "Cellulose nanofibers", which can be divided into "Cellulose nanocrystals" (CNC) having a width of 3-10 nm and L/D >5, and "Cellulose nanofibrils" (CNF or NFC), having a width of 5-30 nm and L/D >50.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low, low viscosity vs. high viscosity etc. The fibrillation technique and the chemical pre-modification have an influence on the fibril size distribution. Typically, non-ionic grades have wider fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood (HW) vs. softwood (SW) pulp, different polysaccharide composition exists in the final nanofibrillar cellulose product. Commonly, the non-ionic grades are prepared from bleached birch pulp, which yields high xylene content (25% by weight). Modified grades are prepared either from HW or SW pulps. In those modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

In an aqueous environment, a dispersion of cellulose nanofibers forms a viscoelastic hydrogel network. The gel is formed at relatively low concentrations of, for example, 0.05-0.2% (w/w) by dispersed and hydrated entangled fibrils. The viscoelasticity of the NFC hydrogel may be characterized, for example, with dynamic oscillatory rheological measurements.

The nanofibrillar cellulose hydrogels exhibit characteristic rheological properties. For example they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives several successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one embodiment the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be, for example, Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material in the method may be characterized by the viscosity it provides in a water solution. The viscosity describes, for example, the fibrillation degree of the nanofibrillar cellulose. In one embodiment the nanofibrillar cellulose when dispersed in water provides a Brookfield viscosity of at least 2000 mPa·s, such as at least 3000 mPa·s, measured at a consistency of 0.8% (w/w) and at 10 rpm. In one embodiment the nanofibrillar cellulose, when dispersed in water, provides a Brookfield viscosity of at least 10000 mPa·s measured at a consistency of 0.8% (w/w) and at 10 rpm. In one embodiment the nanofibrillar cellulose, when dispersed in water, provides a Brookfield viscosity of at least 15000 mPa·s measured at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at a consistency of 0.8% (w/w) and at 10 rpm.

In one embodiment the nanofibrillar cellulose comprises non-modified nanofibrillar cellulose. In one embodiment the nanofibrillar cellulose is non-modified nanofibrillar cellulose. It was found out that the drainage of non-modified nanofibrillar cellulose was significantly faster than with for example anionic grade. Non-modified nanofibrillar cellulose generally has a Brookfield viscosity in the range of 2000-10000 mPa·s, measured at a consistency of 0.8% (w/w) and at 10 rpm.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, that is, pulp.

The modification treatment to the fibers may be chemical or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface. The modification treatment may also be enzymatic.

The cellulose in the fibers may be especially ionically charged after the modification, because the ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. A cationic charge in turn may be created chemically by cationization by attaching a cationic group to the cellulose, such as quaternary ammonium group.

In one embodiment the nanofibrillar cellulose comprises chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the nanofibrillar cellulose is cationically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose. Chemically modified nanofibrillar celluloses may be used to affect to the release profile of certain active agents. For example anionic grades may be used to release cationically charged molecules to obtain a prolonged release rate, or vice versa.

The cellulose may be oxidized. In the oxidation of cellulose, the primary hydroxyl groups of cellulose may be oxidized catalytically by a heterocyclic nitroxyl compound, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

In one embodiment such chemically modified nanofibrillar cellulose, when dispersed in water, provides a Brookfield viscosity of at least 10000 mPa·s measured at a consistency of 0.8% (w/w) and at 10 rpm. In one embodiment such chemically modified nanofibrillar cellulose, when dispersed in water, provides a Brookfield viscosity of at least 15000 mPa·s measured at a consistency of 0.8% (w/w) and at 10 rpm. In one embodiment such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one embodiment the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at a consistency of 0.8% (w/w) and at 10 rpm.

In one embodiment the nanofibrillar cellulose comprises chemically unmodified nanofibrillar cellulose. In one embodiment such chemically unmodified nanofibrillar cellulose, when dispersed in water, provides a Brookfield viscosity of at least 2000 mPa·s, or at least 3000 mPa·s, measured at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one embodiment said nanofibrillar cellulose has a number average diameter of a fibril in the range of 1-100 nm. In one embodiment said nanofibrillar cellulose has a number average diameter of a fibril in the range of 1-50 nm, such as 5-30 nm. In one embodiment said nanofibrillar cellulose has a number average diameter of a fibril in the range of 2-15 nm, such as TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s−1 is exceeded. This method may be used for determining the zero-shear viscosity.

In one example the nanofibrillar cellulose, when dispersed in water, provides a zero shear viscosity ("plateau") of constant viscosity at small shearing stresses) in the range of 1000-100000 Pas, such as in the range of 5000-50000 Pas, and a yield stress (shear stress where the shear thinning begins) in the range of 1-50 Pa, such as in the range of 3-15 Pa, determined by rotational rheometer at a consistency of 0.5% (w/w) by weight in aqueous medium.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at a consistency of 0.8% (w/w) and at 10 rpm.

The starting material for the preparation process is usually nanofibrillar cellulose obtained directly from the disintegration of some of the above-mentioned fibrous raw material and existing at a relatively low concentration homogeneously distributed in water due to the disintegration conditions. The starting material may be an aqueous gel at a concentration of 0.2-10%.

In one embodiment the concentration of the nanofibrillar cellulose in the hydrogel before the freeze-drying is 10% (w/w) or less, or less than 10% (w/w), such as in the range of 0.1-10% (w/w), 0.1-5% (w/w), 0.1-2% (w/w), or 0.1-1.0% (w/w). A preferable range useful for cell culture applications is 0.1-2% (w/w), 0.1-1% (w/w) or 0.5-1% (w/w). With a concentration below 0.5% (w/w) many cells do not grow as spheroids in 3D culture. On the other hand, a concentration of 1.0% (w/w) or more is too high for many cells. The same concentrations of the hydrogels may be restored after freeze-drying from the freeze-dried gels. More particularly dried gel is redispersable in water and will give, when redispersed in water, for example at a dispergation concentration in the range of 0.1-10% (w/w), such as in the ranges disclosed in previous, a viscosity profile that is equal or substantially equal to the viscosity profile it had originally at the same dispergation concentration.

Cryo- and Lyoprotectants

Cryoprotectants (which may be also called as excipients or cryoprotective agents) contribute to the preservation of the structures of proteins, liposome bilayers and other substances during freezing in general. Lyoprotectants stabilize these substances during drying, especially freeze-drying. In freeze-drying lyoprotectant may be also considered as a cryoprotectant, so as used herein the term "cryoprotectant" may also include lyoprotectants. Protective additives can be generally considered to have two types: (i) amorphous glass forming, and (ii) eutectic crystallizing salts. Examples of lyoprotectants include polyhydroxy compounds such as sugars (mono-, di-, and polysaccharides), trehalose and sucrose as natural lyoprotectants and polyalcohols, such as glycerol, and their derivatives. Both of these groups belong to the type (i). Not all cryoprotectants are suitable compounds as lyoprotectants, however. For example, in the cryopreservation of cells, DMSO is commonly used as a cryoprotectant as up to 5% (v/v). However, as it is an organic solvent, its usage in freeze-drying is limited due to evaporation, as its freezing point in solutions is relevantly high. Therefore the use of DMSO as cryoprotectant is not desired in the present method.

In one embodiment the method comprises providing one or more cryoprotective and/or lyoprotective agent(s). In one embodiment the method comprises providing at least one lyoprotective agent, preferably in addition to the nanofibrillar cellulose hydrogel. In one embodiment the method comprises providing at least one cryoprotective and lyoprotective agent(s), which may be the same agent, such as trehalose or PEG, or different agents. One group of cryoprotective agent(s) include alcohols containing at least two hydroxyl groups, such as glycols, for example ethylene glycol, propylene glycol and glycerol. It was discovered that useful cryoprotective agent(s) for cells include trehalose, glycerol and polyethylene glycol (PEG). In one embodiment the one or more cryoprotective and/or lyoprotective agent(s) is selected from trehalose, glycerol, and polyethylene glycol. In one embodiment the cryoprotective and/or lyoprotective agent comprises trehalose. In one embodiment the cryoprotective and/or lyoprotective agents comprise trehalose and glycerol. This combination was discovered to provide especially good cryo- and lyoprotection for cells in a NFC hydrogel matrix. In one embodiment the cryoprotective and/or lyoprotective agents comprise trehalose and polyethylene glycol. In one embodiment the cryoprotective and/or lyoprotective agent(s) comprise glycerol and polyethylene glycol. In one embodiment the cryoprotective and/or lyoprotective agent(s) comprise trehalose, glycerol and polyethylene glycol. Trehalose, also known as α,α-trehalose; α-D-glucopyranosyl-(1→1)-α-D-glucopyranoside, mycose or tremalose, is a natural alpha-linked disaccharide formed by an α,α-1,1-glucoside bond between two α-glucose units. Trehalose is nutritionally equivalent to glucose, because it is rapidly broken down into glucose by the enzyme trehalase. Trehalose may be present as anhydrous or as dihydrate. In one embodiment the trehalose is D(+)-trehalose dehydrate, which is compatible with nanofibrillar cellulose. In one example the trehalose is D-(+)-trehalose dehydrate. It may be provided as solid or as dissolved in an aqueous medium, such as water. Trehalose was found out to act as both cryoprotective and lyoprotective agent for cells in nanofibrillar cellulose hydrogel.

Glycerol is a simple polyol compound. It is a colorless, odorless, viscous liquid that is sweet-tasting and non-toxic. The glycerol backbone is found in all lipids known as triglycerides. Glycerol has three hydroxyl groups that are responsible for its solubility in water and its hygroscopic nature. Glycerol was found out to act mostly as a cryoprotective agent for the cells in nanofibrillar cellulose hydrogel.

Polyethylene glycol (PEG) is a polyether compound also known as polyethylene oxide (PEO) or polyoxyethylene (POE), depending on its molecular weight. The structure of PEG is commonly expressed as H—(O—$CH_2$—$CH_2$)n-OH. In general polyethylene glycols are prepared by polymerization of ethylene oxide and are commercially available over a wide range of molecular weights from 300 g/mol to 10000000 g/mol. Polyethylene glycol is water-soluble and it has a low toxicity. Polyethylene glycol was found out to act as both cryoprotective and lyoprotective agent for cells in nanofibrillar cellulose hydrogel.

In one embodiment the polyethylene glycol has a molecular weight in the range of 100-10000 kDa, such as 1000-10000 kDa. In one embodiment the polyethylene glycol has a molecular weight in the range of 3000-8000 kDa, such as 5000-7000 kDa, for example about 6000 kDa. A "molecular weight" as used in this disclosure may refer to number average molar mass. In general the number average molecular mass of a polymer can be determined for example by gel permeation chromatography, viscometry via the (Mark-Houwink equation), colligative methods such as vapor pressure osmometry, end-group determination or proton NMR.

Preparation of the Freeze Dried Product

The method comprises providing the ingredients nanofibrillar cellulose, in general as an aqueous suspension or hydrogel, cells, and the desired cryo- and/or lyoprotectant(s). In one embodiment the nanofibrillar cellulose is the only cellulosic material in the aqueous suspension or in the hydrogel. In one embodiment the nanofibrillar cellulose is the only polymeric gel-forming material in the aqueous suspension or in the hydrogel. In one example the aqueous suspension or the hydrogel comprises an amount of another fibrous material, such as non-nanofibrillar cellulose, for example an amount in the dried hydrogel (w/w) of the dry weight of the fibrous material.

The method comprises providing a hydrogel comprising nanofibrillar cellulose. The concentration of the nanofibrillar cellulose in the hydrogel may in the range of 0.1-10% (w/w), 0.1-10% (w/w), 0.1-5% (w/w), 0.1-2% (w/w), or 0.1-1.0% (w/w). A preferable range useful for cell culture applications is 0.1-2% (w/w), 0.1-1% (w/w) or 0.5-1% (w/w).

The cells are combined with the hydrogel comprising nanofibrillar cellulose to form a cell system. The cells may be cultured in the cell system. In one example the cells are combined with the hydrogel comprising nanofibrillar cellulose to form a cell culture. A suitable cell culture medium is provided.

The "cell culture medium", "culture medium", "medium", as used herein for use with cells, refers to any suitable medium which is adapted to be compatible with cells. Such medium is usually liquid aqueous and contains auxiliary agents, such as nutrients, salts, vitamins, and/or other agents such as hormones, growth factors and the like. Blood serum or synthetic serum may be included. The medium may be used for culturing the cells, for suspending the cells, and/or for rehydrating the dried gel/cells. Preferably the medium does not contain calcium or magnesium.

The method comprises providing one or more cryoprotective agent(s), such as one or more cryoprotective and/or lyoprotective agent(s), for example in a culture medium, and adding the one or more cryoprotective agent(s) to the cell system or to the cell culture. For example the cell culture medium may be changed into medium containing one or more cryoprotective and/or lyoprotective agent(s). The hydrogel comprising nanofibrillar cellulose may be provided as containing one or more cryoprotective and/or lyoprotective agent(s), such as at least trehalose.

In one example the cryoprotective and/or lyoprotective agent(s) comprise trehalose and glycerol, wherein the concentration of trehalose in the culture medium may be in the range of 0.2-0.5% (w/w) and the concentration of glycerol in the culture medium may be in the range of 0.5-1.5% (w/w), for example about 0.3% (w/w) of trehalose and 1% (w/w) of glycerol. The gel concentration may be in the range of 0.3-1.0% (w/w), such as 0.3-0.5% (w/w).

In case of glycerol and trehalose as cryoprotective and/or lyoprotective agents, the ratio of dry nanofibrillar cellulose in the gel to the cryoprotectants (NFC:glycerol:trehalose by weight) may be for example about 9.5:3:1 to 20:3:1. In some examples the ratio of dry nanofibrillar cellulose in the gel to the cryoprotectants (NFC:glycero:trehalose) is in the range of 5-40:2-6:1 by weight, 9-22:2-6:1 by weight, or 9.5-20:2-5:1 by weight, or 9-22:2-4:1 by weight, or 9.5-20:2-4:1 by weight, for example about 10:5:1 by weight or about 10:5:1 by weight, about 15:5:1 by weight, about 10:3:1 by weight, about 15:3:1 by weight or about 20:3:1 by weight.

Alternatively, or in addition, the one or more cryoprotective and/or lyoprotective agent(s) may be added to the cell culture medium in the cell culture. The concentrations explained in previous may be obtained in the medium. In one example trehalose is included in the culture medium first and the cells are incubated with trehalose for a period of time, for example for about 12-24 hours, for example with 20-100 mM trehalose medium, before other cryoprotectants are added.

The obtained mixture, gel, cell system, extracellular vesicle system or cell culture is freeze-dryable, i.e. the freeze-drying process does not have remarkable effect to the physical properties of the dried nanofibrillar gel, the vesicles or the cells. The mixture may be also called as a freeze-dryable hydrogel. One example of such physical property of the hydrogel is a release profile of an agent from the hydrogel, such as small or large molecule(s), for example therapeutic agent(s). It was found out that different molecules having a variety of molecular weights, including relatively small organic molecules as well as larger proteins, could be released from the hydrogel in a controlled way with similar release profile. The useful molecular weight range is very broad, for example in the tests molecules having a molecular weight in the range of about 170-70 000 g/mol (Daltons) could be released controllably. However, the molecules with high molecular weight did release slower than the molecules with lower molecular weight. One example of such physical property of the cells is the integrity of the cells, such as preservation of cell membranes, cell organelles, microvesicles, and/or other parts of the cells. Another example of the physical property of cells is the three-dimensional form of the cell colony.

In one embodiment the method comprises providing one or more therapeutic or other active agent(s) and mixing the agent(s) with the hydrogel, optionally cryoprotective and/or lyoprotective agent(s) and/or the cells, for example adding the agent(s) to the medium. The agent(s) may be added simultaneously with the one or more cryoprotectant(s), or the agents(s) may be added before or afterwards. Similarly any other additives may be provided and mixed with the hydrogel or the medium, such as chemical(s), nutrient(s), cell culturing agent(s) and the like.

After the cell system or the vesicle system has been obtained, it is freeze-dried to obtain a dried hydrogel, or more particularly an aerogel, comprising nanofibrillar cellulose. Any suitable freeze-drying method may be used. Freeze drying, which may also be called as lyophilisation, is a method which uses rapid cooling to produce thermodynamic instability within a system and cause phase separation. The solvent is then removed by sublimation under vacuum leaving behind voids in the regions it previously occupied. Sublimation refers to transition of a substance directly from the solid to the gas phase without passing through the intermediate liquid phase. Sublimation is an endothermic phase transition that occurs at temperatures and pressures below a substance's triple point in its phase diagram.

In one embodiment the freeze drying comprises first lowering the temperature of the cell system to at least to $-30°$ C., such as at least $-40°$ C., for example to the range of $-30$--$100°$ C., or to the range of $-40$--$100°$ C., or even to about $-200°$ C. or below, for example when using liquid nitrogen, and after that applying lowered pressure to remove water from the cell system. In general the cell system should be frozen before applying the lowered pressure. In one embodiment the temperature is increased during applying lowered pressure and after applying the lowest pressure, for example the temperature is increased to about $-20°$ C. or even to about $10°$ C. The temperature may be increased before the lowered pressure is applied, or it may be increased during applying the lowered pressure.

In one example the freeze drying is carried out by freezing the cell system with liquid nitrogen. For example a vial containing the cell system is dipped into liquid nitrogen until the cell system is frozen. In another example, which yielded better vitrification in the tests, the cells are pipetted directly into liquid nitrogen. After this the lowered pressure is applied to the cell system to remove water from the cell system. The lowered pressure may refer to vacuum required to obtain the sublimation of the water. As the sublimation of the water takes place under the triple point, the required vacuum pressure is dependent on the used temperature. The vesicle systems may be freeze-dried using the same procedure.

"Drying" as used herein refers in general to dewatering, which terms may be used interchangeably, wherein water is removed from a hydrogel to obtain dried or dewatered hydrogel. In one embodiment the freeze drying is continued until the hydrogel has a desired moisture content or the freeze drying is continued to a minimum moisture content, preferably below 20%, or more preferably below 10%, or even below 5%, for example to a moisture content in the range of 1-20%, 2-20%, or 2-10% (w/w). In one embodiment the freeze drying is continued until the hydrogel has moisture content in the range of 1-8%, 2-8%, 2-6%, 2-5% or 1-5% (w/w). In general it may be challenging to obtain moisture content below 2%. After the low moisture content has been obtained, the dried product may be packed into a package in vacuum or in protective gas. This will prevent the dried hydrogel absorbing the ambient moisture, which might raise the moisture content to a range of for example 4-8%, or 5-7% (w/w). The moisture content may be also called as water content. The obtained dried hydrogel may be regelled by adding aqueous liquid, such as culture medium, and suspending the dried product. A regelled or resuspended hydrogel is obtained, which may have the same concentration and water content as before drying. This hydrogel provides characteristics which are substantially equal to the characteristics of the original hydrogel before drying.

Final freeze-dried hydrogels, more particularly freeze-dried aerogels, comprising nanofibrillar cellulose comprising the cells are obtained with the freeze-drying methods of the embodiments disclosed herein. The freeze-dried aerogels may be stored in sealed packages or containers. Inert gas may be provided, such as argon. The freeze-dried products may be stored at lowered temperature, such as in a refrigerator, for example at 0-10° C., such as at about +4° C., or even at room temperature.

One embodiment provides a freeze-dried aerogel comprising nanofibrillar cellulose, cells and one or more cryoprotective and/or lyoprotective agent(s), wherein the moisture content of the hydrogel is 10% or less (w/w), preferably in the range of 2-10% (w/w), such as 2-8% (w/w), as discussed in the previous. The freeze-dried aerogel may further comprise one or more therapeutic or other active agent(s), or other agents, as discussed herein. Actually such a product is no longer in a form of a gel, which in the case of nanofibrillar cellulose generally has a moisture content over 80% (w/w), or over 90% (w/w), even over 95% (w/w). The freeze-dried (nanofibrillar cellulose) aerogel may be therefore called as freeze dried nanofibrillar cellulose.

One embodiment provides the freeze-dried aerogel comprising nanofibrillar cellulose, wherein the content of the cells in the freeze-dried aerogel is in the range of 0.1-65% (w/w), such as of 0.1-50% (w/w), such as in the range of 1-25% (w/w), or 1-20% (w/w), 1-10% (w/w), 1-5% (w/w), or 20-65% (w/w), 10-65% (w/w), 5-65% (w/w), 10-50% (w/w), 5-50% (w/w), 5-25% (w/w), 5-20% (w/w), or 5-15% (w/w).

One embodiment provides the freeze-dried aerogel comprising nanofibrillar cellulose, wherein the content of the extracellular vesicles in the freeze-dried aerogel is in the range of 0.1-65% (w/w), such as in the range of 0.1-50% (w/w), such as in the range of 1-25% (w/w), or 1-20% (w/w), 1-10% (w/w), 1-5% (w/w), or 20-65% (w/w), 10-65% (w/w), 5-65% (w/w), 10-50% (w/w), 5-50% (w/w), 5-25% (w/w), 5-20% (w/w), or 5-15% (w/w).

One embodiment provides the freeze-dried aerogel, wherein the content of the one or more therapeutic or other active agent or other chemical in the freeze-dried hydrogel is in the range of 0.1-65% (w/w), or in the range of 0.1-50% (w/w), such as in the range of 1-25% (w/w), or 1-20% (w/w), 1-10% (w/w), 1-5% (w/w), or 20-65% (w/w), 10-65% (w/w), 5-65% (w/w), 10-50% (w/w), 5-50% (w/w), 5-25% (w/w), 5-20% (w/w), or 5-15% (w/w).

In one embodiment the content of the glycerol is in the range of 1-10% (w/w) in the dried hydrogel, such as in the range of 5-10% (w/w). In one embodiment the content of the trehalose is in the range of 0.5-8% (w/w) in the dried hydrogel, such as in the range of 3-4% (w/w). In one embodiment the content of the polyethylene glycol is in the range of 1-10% (w/w) in the dried hydrogel, such as in the range of 5-10% (w/w). Also combinations of these cryoprotectants and ranges may be used.

In one embodiment the content of the glycerol is in the range of 1-10% (w/w) and/or the content of the trehalose is in the range of 0.5-8% (w/w) in the dried hydrogel. In one embodiment the content of the glycerol is in the range of 5-10% (w/w) and/or the content of the trehalose is in the range of 3-4% (w/w) in the dried hydrogel.

In one embodiment the content of the polyethylene glycol is in the range of 1-10% (w/w) and/or the content of the trehalose is in the range of 0.5-8% (w/w) in the dried hydrogel. In one embodiment the content of the polyethylene glycol is in the range of 5-10% (w/w) and/or the content of the trehalose is in the range of 3-4% (w/w) in the dried hydrogel.

The dried hydrogel may be provided as sheets, blocks or other shapes or forms, in general suitable for the desired purpose, and which may be then rewetted or rehydrated before. The dried hydrogel may also be provided as powder or in other crushed form. In such case the method of preparing the product may contain a step of forming the powder, for example by grinding or crushing the freeze-dried product.

The obtained hydrogels, before or after drying, or more particularly after regelling, may be used in variety of applications, such as those described herein, for example in a method for providing, storing and/or culturing cells. The hydrogel may be provided for example as a medical or a scientific product.

The rehydration or regelling may be carried out by providing aqueous rehydration liquid, which may contain further agents, preferably sterilized liquid. In one example the rehydration liquid comprises or is cell culture medium. The rehydration liquid may be provided as warmed, such as warmed to a temperature in the range of 30-40° C., such as about 37° C. The dried hydrogel containing the cells may be contacted with the liquid and incubated for a period of time, such as for 10-60 minutes, before any further actions.

EXPERIMENTAL PART

Cell Viability Assays

There is no simple in vitro test that could predict cell function after freezing in vivo. The cell viability assays must be specifically aimed at the components of each system that are damaged in the particular circumstances under. Table 1 displays the main components of cell viability tracking. From these, six factors were chosen for the experimental part of this work.

TABLE 1

Classification of Viability Assays. Highlighted methods were chosen as means of analysis for the experimental part of this work.

I. Physical integrity
    1. Gross (i) Appearance
            (ii) Physical property
    2. Microscopic    (i) Light microscopy
            (ii) Electron microscopy
       (iii) CryoEM
II. Metabolic activity
    1. Uptake of metabolites
    2. Production of catabolites

TABLE 1-continued

Classification of Viability Assays. Highlighted methods were chosen as means of analysis for the experimental part of this work.

3. Labile metabolites
    4. Enzymatic reactions        (i) Intracellular
                                  (ii) Membrane transport
III. Mechanical activity
    1. Motility
    2. Phagocytosis
    3. Contraction
    4. Attachment
    5. Aggregation
IV. Mitotic activity
    1. Mitotic index
    2. DNA synthesis
    3. "Plating" tests
    4. Growth and development     (i) Tissue culture
                                  (ii) Embryonic
V. Complete in vivo function
    1. Fertilization and development
    2. Transplantation            (i) Cells
                                  (ii) Tissues
                                  (iii) Vascularized organs The gross appearance of the cells is typically observed with a light microscopy unit at each step of the experiment. CryoEM can also be used to image moist cell cultivations, however the sample is lost in the process, as with SEM imagining.

The metabolic activity of the cells can be quantified with the AlamarBlue® Cell Viability Assay, which is a non-toxic, stable and water-soluble dye. The active ingredient of alamarBlue® reagent is resazurin which is blue in color, and nearly non-fluorescent. It is a cell permeable compound, and inside cells reduced to resorufin, a compound that is red in color and highly fluorescent. This reduction increases the overall red color and fluorescence of the media surrounding the cells. Hence, the cells can be monitored continuously and the increase in fluorescence measured as a function of time. Due to this, the alamarBlue® assay has been considered superior to several other assays for cell viability that required killing the cells, such as the activity of cells oxidoreductase enzymes measuring MTT assay (3-(4,5-dimethylthiazol-2-yl)-2,5-diphenyltetrazolium bromide, yellow tetrazol).

The active compound of alamarBlue® is resazurin, which is indigo blue in color, and will enter the cytosol of cells when added to cell culture samples by active intake. The mitochondrial enzyme activity converts it to resorufin by accepting electrons from NADH (the reduced form of nicotinamide adenine dinucleotide) as visualized in FIG. 8. In addition to NADH, resorufin is also converted by accepting electrons from nicotinamide adenine dinucleotide phosphate (NADPH), hydroquinone form of flavin adenine dinucleotide (FADH), reduced form of flavin mononucleotide (FMNH) and the cytochromes. The redox reaction changes the color of the culture medium to fluorescent pink and this change can be visually observed, but more importantly, accurately measured by fluorometric reading.

The alamarBlue® assay can also be implemented to measure the viability of 3D cell spheroid cultures directly in GrowDex®. In their work, they used ultra-low attachment 96-well plates manufactured by Corning Inc. to cultivate the hydrogel-cell systems, and then used the alamarBlue® Cell Viability Reagent by Invitrogen as 1/10 of the co-volume of medium and hydrogel. As control samples, they used hydrogel systems without cells.

Another, yet more simple method to evaluate the cell viability is cell attachment. Many cell lines attach themselves to suitable surfaces in vitro such as polypropylene or glass, when correct circumstances are applied. The cells achieve this by excreting ECM proteins, such as fibronectin, collagen and laminin that are capable of sticking to rough surfaces. Obviously, dead cells do not excrete these proteins and hence do not actively attach themselves to these surfaces. Single cells typically undergo apoptosis instead of attaching themselves, but in the case of cancerous cell lines, this function has been disabled. Hence it can be derived that cell attachment can be used as a viability assay on cancer cell lines on compatible surfaces.

One method to evaluate the cell membrane integrity is enzyme activity assays combined with nuclei staining. Calcein AM (acetoxy methyl) ester and propidium iodide are suitable for viability assessment of different microbes. Calcein AM is itself a non-fluorescent and cell membrane permeable molecule, but undergoes an esterase reaction when in cytosol if correct enzymes are available and transforms into calcein, which is a fluorescent molecule. This way, the fluorescent cells can be visually observed with fluorescence microscopy or a plate reader.

Another aspect of the dual stain is propidium iodide (PI), a compound that is not cell membrane permeable and hence only enters the cytosol if the cell membrane has been damaged. Therefore, only necrotic cells are affected, whereas apoptotic and healthy cells not. Once in the cytosol, the PI binds to any available DNA and RNA, including the DNA in nucleus. When excited with 535 nm light, an emission of 617 nm can be observed on the areas of dead cells.

Rapid cooling was chosen as the freezing the method for the NFC-cell hydrogel systems. A droplet size of 20 µl was chosen for the step, where the NFC-cell hydrogel is in direct contact with liquid nitrogen. For lyoprotection, trehalose and glycerol were used.

Diluted media was chosen as the rehydration fluid. Four factors were chosen for the determination of the cell viability. Cell attachment was chosen due to the overall picture on viability it provides, while cell morphology is examined in each step with light microscopy. Resorufin oxidation was chosen as the method to evaluate the mitochondrial activity of the spheroids in NFC, the fluorescent dual Cellstain to determine the viability of the cells trough enzyme activity and cell membrane integrity. Hep G2 cells were cultivated in GrowDex®.

The GrowDex® hydrogel forms a supporting matrix around the cells and provides adjustable pressure and support that induces growth of 3D cell systems. GrowDex® can be adjusted in several ways to fulfil the requirements of different cell types and to current date, GrowDex® has been successfully optimized as a 3D cell culture matrix for six different types of cells; HepaRG, ARPE-19, MUG-Mel2 and Hep G2 cell lines, and WA07 and iPS(IMR90)-4 stem cell lines.

Materials 1.5% (lot 11792) NFC hydrogel (GrowDex®) was obtained from UPM-Kymmene Oyj, Finland. The diameter of most of the fibrils was in the range of 4-10 nm and the length in the range of 500-10 000 nm. All other compounds used were of analytical grade and either sterilized by UV light or filtration prior to implementation. D-(+)-trehalose dehydrate, low adhesion 96-well inertGrade BRANDplates®, Cellstain double staining kit, fetal bovine serum and glycerol (99%) were purchased from Sigma-Aldrich, USA. Polyethylene glycol (Mn 6000) was purchased from Fluka, Switzerland. Penicillin-streptomycin solution (Pen-Strep, 10 000 U/ml), Dulbecco's modified eagle media (DMEM) without magnesium and calcium and Dulbecco's Phosphate Buffered Saline (DPBS) 10× concentrate without magnesium and calcium were purchased from Gibco, UK. Liquid nitrogen used in vitrification and argon gas used in preservation were purchased from AGA Industrial Gases, Finland. MycoAlert™ Mycoplasma Detection Kit was bought from Lonza, Switzerland. PS SensoPlate™ 96 well glass bottom plates for confocal imagining were purchased from Greiner Bio-One, Austria. Sterile Corning® breathable sealing tape was purchased from Corning, USA. The human hepatocellular carcinoma Hep G2 cells (passage number 100, ATCC HB-8065) were purchased from ATCC®, USA. TrypLE Express and alamarBlue® Cell Viability Reagent by Invitrogen was purchased from Thermo Fisher Scientific. All solutions used were made in double distilled ultrapure water.

Pulp obtained from birch tree is used as a material when producing the GrowDex® hydrogel. First, the pulp is purified and bleached. Next, the cellulose fibers are dispersed in double distilled ultrapure water and isolated in order to form a homogenous hydrogel. Lastly, the obtained hydrogel is sterilized by autoclaving it in 121° C. for 20 minutes.

Methods

Cultivating 3D Cell Spheroids from Hep G2 Cancerous Liver Cell Line

Hep G2 cancerous cell line was selected for the experiments as it is a well characterized and a strong cell line, and has provided repeatable and reliable results in previous studies concerning cultivation in NFC hydrogel. During the study, the cell line was cultivated with and without GrowDex® in order to obtain a control sample to differentiate the effects of NFC in the survivability. 3D cell spheroids grown in 0.8% (w/w) GrowDex® are displayed in FIG. 1. Images (A), (B) and (C) display typical spheroids with a diameter between 100 and 120 µm. However, the image (D) shows a larger spheroid with a diameter over 160 µm. Typically the spheroids do not grow to this large size in 5 days, implying that there was an cell aggregate at the seeding phase. The growth was limited to 5 days, to avoid too large spheroids, as nutrients and oxygen cannot diffuse to the core of a spheroid once it has reached a large size enough.

On top of 2D and 3D cultivations, an upkeep line was cultivated in cell flasks as a source of fresh cells for each new 2D and 3D seeding. The upkeep bottle was split twice a week from passage numbers 100 to 152. The properties of Hep G2 cells have been studied to be unchangeable at high passage numbers by ATCC. When the upkeep bottle was split for the passage, the cells were first washed twice with 1×DPBS, detached with 4 ml of tryple and reseeded to 75 cm$^2$ flasks with 11-14 ml of fresh media. The media contained 90% (v/v) of DMEM without calcium and magnesium and 10% (v/v) of FBS for growth factors. In the 3D seeding phase, the cells were spun in a centrifuge at 200 RCF (relative centrifugal force) for 6 minutes and the formed supernatant was removed. Fresh media was added, and the cells were mixed with GrowDex® to create a 3D cell system containing 0.8% (w/w) of NFC. An equal volume of fresh media was added as a separate layer to provide nutrition and moisture. The cell plates were then stored in an incubator at +37° C. and with 5% of $CO_2$ for 4 days.

The cell medium (DMEM) contains phenol red, which gives a red color to the media. Samples (B) and (C) in FIG. 1 were imaged without the media layers (as they were vitrified without the media) resulting in a more yellow background.

Optimization of Lyoprotectants

Three lyoprotectants were chosen for testing with GrowDex®. First, the cells were cultivated regularly for 4 days either in 2D or 3D with 0.8% (w/w) of GrowDex®, and then the medium was changed. For some of the samples the medium was replaced with medium containing 50 mM of trehalose dihydrate and possibly glycerol or PEG 6000, while others received only regular medium. On day 5, the medium layer was mixed by pipetting with the hydrogel layer in order to form 0.4% (w/w) hydrogel. In the case of 2D cells, the cells were detached with triple prior to freezing. All systems were frozen rapidly by injecting the mixture as 20 µl droplets to liquid nitrogen. Then, the systems were freeze-dried and rehydrated and evaluated for viability with Cellstain double staining and fluorescence microscopy. Table 2 demonstrates all of the optimization combinations and their evaluated viabilities.

TABLE 2

Optimization chart for lyoprotectants and viabilities after rehydration based on Cellstain double staining.

| Lyoprotectants | PEG 6000 0.7% (w/w) | Trehalose 0.3% (w/w) | Glycerol 1% (w/w) | Viability (LIVE/DEAD) |
|---|---|---|---|---|
| GrowDex ® 0.8% (w/w) & 24 h trehal. incub. | x | x | x | ++ |
| GrowDex ® 0.8% (w/w) & 24 h trehal. incub. | x | x |   | + |
| GrowDex ® 0.8% (w/w) & 24 h trehal. incub. | x |   |   | + |
| GrowDex ® 0.8% (w/w) & 24 h trehal. incub. |   |   | x | ++ |
| GrowDex ® 0.8% (w/w) & 24 h trehal. incub. |   | x | x | ++ |
| GrowDex ® 0.8% (w/w) & 24 h trehal. incub. |   | x |   | + |
| GrowDex ® 0.4% (w/w) & 24 h trehal. incub. | x | x | x | +++ |
| GrowDex ® 0.4% (w/w) & 24 h trehal. incub. | x | x |   | ++ |
| GrowDex ® 0.4% (w/w) & 24 h trehal. incub. | x |   |   | ++ |
| GrowDex ® 0.4% (w/w) & 24 h trehal. incub. |   |   | x | ++ |
| GrowDex ® 0.4% (w/w) & 24 h trehal. incub. |   | x | x | +++ |
| GrowDex ® 0.4% (w/w) & 24 h trehal. incub. |   | x |   | ++ |
| GrowDex ® 0.8% (w/w) | x | x |   | + |
| GrowDex ® 0.8% (w/w) |   | x |   | + |
| GrowDex ® 0.8% (w/w) |   |   |   | + |
| Without GrowDex ® | x | x |   |   |
| Without GrowDex ® |   | x | x |   |
| Without GrowDex ® |   | x |   |   |
| Without GrowDex ® & 24 h treha. Incub. | x | x |   |   |

TABLE 2-continued

Optimization chart for lyoprotectants and viabilities after rehydration based on Cellstain double staining.

| Lyoprotectants | PEG 6000 0.7% (w/w) | Trehalose 0.3% (w/w) | Glycerol 1% (w/w) | Viability (LIVE/DEAD) |
|---|---|---|---|---|
| Without GrowDex ® & 24 h treha. Incub. | | x | x | |
| Without GrowDex ® & 24 h treha. Incub. | | x | | |

Great results were obtained with the Cellstain from two combinations. The first mixture contained 0.4% (w/w) of GrowDex®, 1% (w/w) of glycerol, 0.3% (w/w) of trehalose and it had been exposed to 50 mM trehalose medium for 24 hours. The next mixture contained the same substances but in addition PEG 6000 (0.7% (w/w)). Therefore, it was concluded that PEG 6000 had most likely no or little role in the lyoprotection of the mixture. All the experiments from here on were performed with the first mixture (0.4% (w/w) of GrowDex®, 1% (w/w) of glycerol, 0.3% (w/w) of trehalose and 24 h trehalose incubation).

Addition of the Lyoprotectants and Trehalose Incubation

After cultivating the cells for 4 days in 0.8% (w/w) GrowDex®, the above layer of media was changed. First, the cell systems were centrifuged at 200 RCF for 6 minutes directly in the 96-well cultivation plates. Next, the supernatant was aspired from each well. Then, a new media mixture containing 50 mM of trehalose dihydrate, 2% (w/w) of glycerol and 1% (v/v) of PenStrep antibiotic mixture was added. The amount of glycerol was double due to the fact that it was scaled against the medium layer, which is only half of the well. Next, the cells were incubated for 24 hours at +37° C. and 5% $CO_2$. During the incubation, the cells in-took part of the trehalose, whilst the glycerol remained in the extracellular space. After the incubation, the diameter of the grown spheroids was measured with a Leica AF light microscope as shown in 10. Finally, the media layer was mechanically mixed with the hydrogel layer by pipetting each sample well back and forth. This ensured that the NFC content was lowered from 0.8% to approximately 0.4% thoroughly, which had earlier been optimized by us as the most suitable NFC amount for the lyoprotective matrix effect (lower concentration of fibers decreases the overall porosity of the sample).

Differential Scanning Calorimetry

Figure 5:
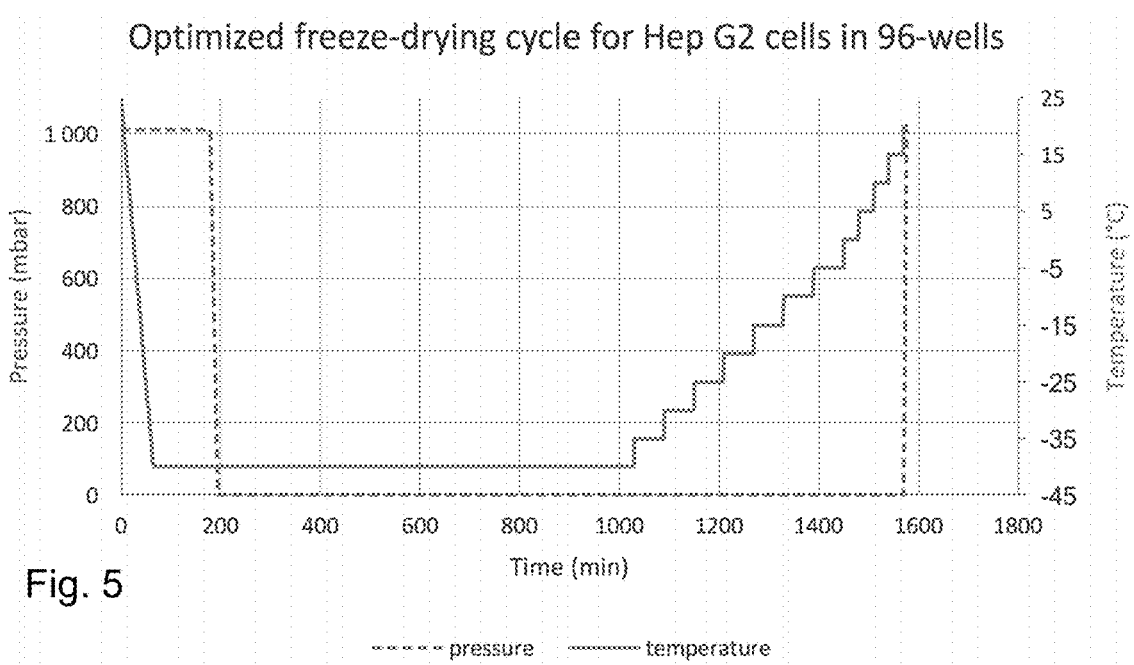
FIG. 5 shows an optimized freeze-drying cycle for Hep G2 spheroid cell systems in GrowDex® in 96-wells (200 µl per well) for EPSILON 1-6D by CHRIST resulting in dry samples with minimum time consumed.

Freezing points (FP) and glass transition points (Tg) were measured from the hydrogel-cell mixtures with differential scanning calorimetry (DSC). The freeze-drying cycle in FIG. 5 was simulated with the DSC with cooling rate of 1° C./min and heating rate 1° C./10 min. In addition, a cooling rate of 5° C./min was used to more distinctly point out the Tg temperatures. Cell-hydrogels with cryoprotectants resulted in FP of −24.75° C. and in −23.75° C. without cells (control). The systems without cryoprotectants resulted in −22.77° C. with cells and in −22.35° C. without cells. Tg' for the trehalose could not be detected even with the accuracy of 0.2 mW, but this is most likely due to the low total amount of trehalose in the samples.

Sterilization of Liquid Nitrogen

Figure 2:
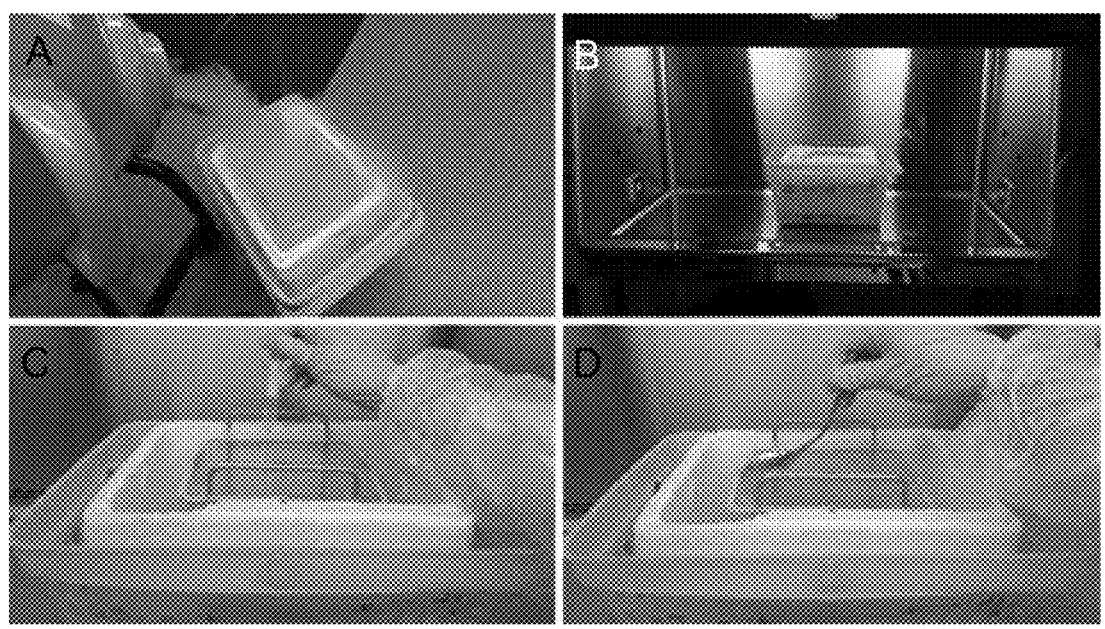
FIG. 2 shows sterilization of liquid nitrogen. (A) Contaminated liquid nitrogen is poured into a clean bucket. (B) 70% Ethanol is used to spray the whole system and it is sterilized in a laminar with UV-C light. (C) Inside the laminar, 15 ml tubes are installed to the rack without caps. (D) The tubes are filled with approximately 5 ml of sterilized liquid nitrogen while the tubes are still submerged in liquid nitrogen.

The liquid nitrogen provided by AGA, Finland, contains contaminants in frozen state, and as the cell samples are pipetted directly into the liquid nitrogen for maximum freezing rate in the vitrification step, the liquid nitrogen had to be sterilized before use. First, the liquid nitrogen was poured into a clean bucket as in FIG. 2 (A) and placed inside an ESCO laminar (DDTC/AU 550305054). Here, (B) it was sterilized by ultraviolet (UV) light for 18 minutes with a dose of 20,000 $\mu W/cm^2$ of UV-C radiation. Next, a custom built metallic rack was submerged into the sterile nitrogen and then 15 ml sterile open tubes (C) were aseptically attached to the rack and hence submerged into the sterile liquid nitrogen. Then, a metal spoon (D) was used to fill the tubes with approximately 5 ml of sterile liquid nitrogen. As the tubes containing liquid nitrogen were submerged in the bucket of nitrogen, evaporation was unnoticeable during the whole working and transportation steps, giving us an ideal working environment for the vitrification step, which was also performed inside the cell laminar. The excessive amount of liquid nitrogen around the tubes also facilitated the transportation of the cell tubes to the freeze-drier, as it kept its temperature well.

Vitrification

In the next step, the cell plates were brought inside the laminar. Each 96-well containing 3D cell spheroid hydrogel were properly mixed by pipetting with low adhesion pipette tips. By mixing the media layer in each well with the hydrogel layer, a new hydrogel mixture with 0.4% (w/w) fiber content was formed. Next, the new hydrogel was carefully pipetted as tiny droplets directly into liquid nitrogen inside the 15 ml tubes as in FIG. 3 (A). This caused the droplets to freeze as small spheres with approximately 2-5 ml diameter. The freezing rate could be visually observed to some extent, as the used media contains phenol red, a compound that switches color from pink to yellow as soon as no liquid water is present. The observed color change from pink to yellow was instant, indicating rapid freezing. Lastly, the rack with the cell tubes was placed inside a freeze-drying chamber (B) while still containing some liquid nitrogen to protect the samples from excessive heat energy.

Freeze-Drying

Figure 4:
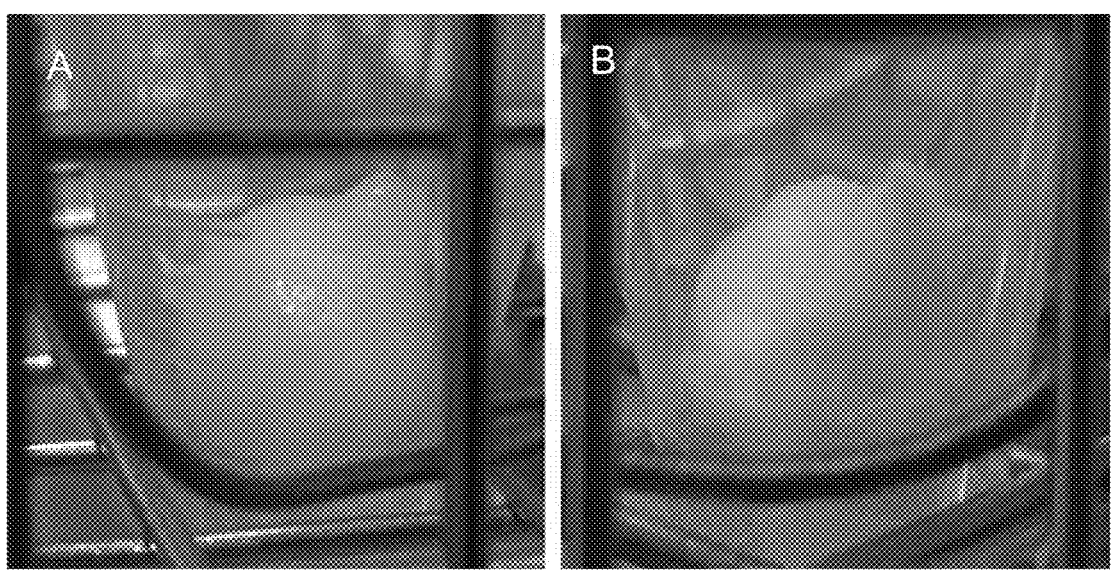
FIG. 4 shows (A) A vitrified 200 µl cell sample in frozen state after rapid freezing. (B) The sample after freeze-drying in dry state.

After vitrification, the freeze-drying process was immediately executed. It was performed in Biocenter 2, Helsinki with ScanVac CoolSafe manufactured by Labogene. The model does not have a separate cooling system for samples and no programmable main unit, so the temperature per time could not be tracked. However, due to phenol red in the cell media, we could exclude the presence of any free water in the samples at the beginning of the freeze-drying cycle, as in the case of yellow sample in FIG. 4 (A). The condenser was kept at −106° C. during the whole process.

Figure 3:
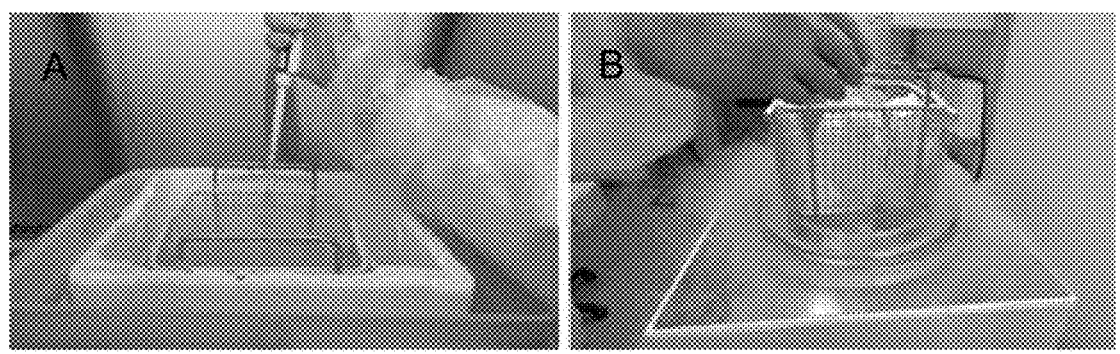
FIG. 3 shows freezing of the cell hydrogels and igniting the freeze-drying. (A) Rapid freezing by pipetting small droplets of cell-hydrogel mixtures directly into liquid nitrogen. (B) Transportation of the samples in liquid nitrogen to the freeze-drier and tubes still containing liquid nitrogen once the vacuum is ignited.

The samples were transported and placed inside the freeze-drier after the vitrification so that the 15 ml tubes still contained 2-3 ml of liquid nitrogen as in FIG. 3 (B). The freeze-drying cycled was immediately initialized, so that the still forming nitrogen gas was collected by the vacuum pump. This ensured the minimum starting temperature for our samples, as the samples typically warm up during the vacuum initializing phase. The vacuum chamber reached a vacuum level of 0.001 mbar in approximately 15 minutes. The freeze-drying cycle was continued for 72 hours, during which the samples warmed at an unknown rate, as the instrument bears no temperature sensors. A thermographic camera was used through the chamber glass, however, it only measured the surface temperature of the chamber instead of the samples. Nevertheless, the observed yellow hue of the phenol red ensured the dryness of the samples at the end as in FIG. 4 (B). The vacuum was slowly released with room air during 5 minutes.

Storage and Recreation

The dried samples were stored in closed plastic tubes secured with Parafilm® and placed inside a desiccator with dried silica balls and filled with argon gas and stored in +4° C. After one day of storage, the samples were aseptically reconstructed with designed rehydration liquid, which was specially designed for the rewetting of the dried NFC systems. In order to avoid the shock from the high concentration differences, a novel rehydration liquid was designed to contain extra media in addition to ultrapure water, so that when added excessively, the original osmotic pressure of the system is achieved. The novel recreation liquid contained 1% (v/v) of PenStrep mixture, 79% (v/v) of autoclaved ultrapure water and 20% (v/v) of media. The rehydration liquid was added to the dried samples so that the liquids volume corresponded 125% (v/v) of the dry samples original wet volume, except 2.5% (v/v) was reduced to correspond to the dry volume of the sample. Hence, by adding 122.5% (v/v) of the recreation liquid, the original osmotic pressure was achieved while 20% (v/v) of fresh extra medium was added. Before addition of the rehydration liquid, it was warmed to +37° C. to ensure a gentle contact with the cells. The liquid was added to the samples by inserting a loaded 1000 µl low adhesion tip inside the 15-ml tube, and rapidly mixed by pipetting. The cells were then placed immediately in an incubator at +37° C. and 5% $CO_2$ for 15 minutes prior any other processing.

Novel Freeze-Drying Cycles Maintaining Sterility

During the research, two novel sterile freeze-drying methods were produced. The first freeze-drying cycle was optimized in Turku University of Applied Sciences for freeze-drying doses of 200 µl of cell hydrogel systems. The instrument was a versatile drier with programmable operating system in Kupittaa, Turku. The operated model was EPSILON 1-6D and manufactured by CHRIST. The instrument had automated and programmable oil-based cooling shelves and a controlled vacuum pump. Therefore, we were able to design a unique freeze-drying cycle for 3D cell hydrogel samples in 96-wells. The final optimized cycle is presented in FIG. 5.

However, the research was later moved to the second freeze-drier in Viikki, Helsinki. This model was ScanVac CoolSafe by Labogene. The model did not have a separate cooling system and no programmable main unit, so, as a result no cycle could be optimized for it. However, it was used to produce all the results of this study. The samples were vitrified with liquid nitrogen and dried in 0.001 mbar pressure for 72 hours.

As both of the used instruments were located in contaminated room air, two new sterile drying methods were developed for this study. The first system in FIG. 6 (A) shows a 235 $cm^2$ cell culturing flask (manufactured by Corning®) cut in two pieces, which have been sterilized and reconnected later in a sterile cell laminar after insertion of a 96-well plate, which has been marked with an arrow. The cap of the bottle has been replaced with a fresh, sterile packed cap inside the laminar.

Next, the junction between the reconnected bottle pieces was made airtight with 70% ethanol wiped Parafilm® and after removal from the laminar, with regular air conditioning tape. The whole flask was then carefully placed inside the freeze-drying chamber, frozen 1° C./minute in a controlled manner and freeze-dried. The 96-well plate contained the cell hydrogel systems, and could only exchange gas molecules through the extensive filter of the cap. Afterwards, the dried samples were tested for contaminations and mycoplasma with MycoAlert™ Mycoplasma Detection Kit. No contaminations or mycoplasma were detected.

Figure 6:
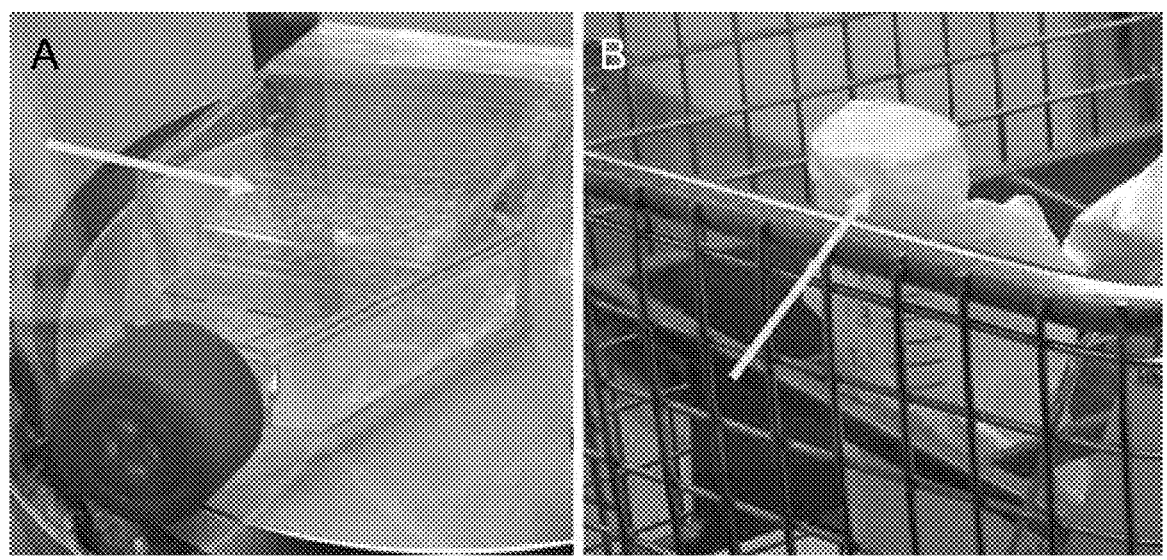
FIG. 6 shows (A) A cell flask containing a 96-well plate with cell samples. (B) A 15 ml tube sealed with sterile Corning® breathable sealing tape.

In FIG. 6 (B), a polypropylene tube is shown tightly closed with a Sterile Corning® breathable sealing tape. As no freeze-drying proof sealing tape was on the market, the manufacturer of this tape (Corning, USA) was contacted and a free sample received. The test results revealed that liquid nitrogen had no effect on the adhesive properties of the tape, and it filtered the air as no contaminants nor mycoplasma were detected afterwards.

Mycoplasma and Sterility Tests

After vitrification, freeze-drying, storage and recreation, the samples were tested for mycoplasma. The recreated cell hydrogel systems were collected and seeded into 25 $cm^2$ culture flasks with 5 ml of media and then cultivated for 8 days. During this time, the cell bottles were observed daily for any changes in media color, scent and appearance of any microscopic activity was observed. No microbiological activity or changes in the media pH or scent were discovered. Next, the media samples were tested for mycoplasma with MycoAlert™ Mycoplasma Detection Kit. It also yielded negative results, and therefore it was concluded that both the Corning® breathable sealing tape and the cell flask cork filters managed to maintain the sterility of the samples during freeze-drying.

Live/Dead Double Staining for Cell Viability

The recreated cell systems were tested for viability with a Live/Dead double staining kit for mammalian cells. The amount of calcein AM and propidium iodide were first optimized with healthy 3D Hep G2 cell cultivations and with 70% ethanol killed cell control samples. Next, the freeze-dried and recreated samples were diluted with DPBS (without calcium and magnesium) buffer so that the final NFC concentration was 0.1%, as during the optimization it was observed that this concentration of NFC or below interrupted the least with the dyes, but the presence of some NFC was required to stabilize the cells for imagining. Spheroids were suspended in staining solution containing Calcein-AM 1:500 (Cellstain double staining kit; Sigma Aldrich) and 50 µg/ml DAPI (Invitrogen, Carlsbad, CA) for 15 min at 37° C., and transferred on a Greiner Sensoplate™ glass bottom 96 well plate (Sigma Aldrich). The fluorescent images were taken with Leica SP5 II HCA microscope using HC PL APO 10x/0.4 (air) and HC PL APO 20x/0.7 CS (air) objectives. Imaris 8.4.1 software was used for acquisition of the images. The possibility for autofluorescence was excluded by dead control samples. First, the freeze-dried and recreated control systems were killed with 70% ethanol in a 30-minute incubation, and then dyed with the same dyes as the samples. No green fluorescence was observed in the control samples.

AlamarBlue® Cell Viability Assay

The mitochondrial metabolic activity of the Hep G2 cell spheroids was determined before and after freeze-drying with an oxidation-reduction indicator, resazurin (alamarBlue® Cell Viability Reagent, manufactured by Invitrogen). First, alamarBlue® was applied as 1/10 of the co-volume of the medium and hydrogel mixture. Then, the cells were exposed to the resazurin for 4 hours at 37° C. in 5% $CO_2$.

Next, the culture plates were centrifuged for 7 minutes at 200 rcf, and 50 ml of the formed supernatant (medium) was transferred from each culture well to a black 96-wellplate. Lastly, the metabolite of the resazurin (fluorescent resorufin) was recorded with a plate reader (Varioskan Flash, Thermo Fisher) using excitation at 560 nm and emission at 590 nm.

Figure 7:
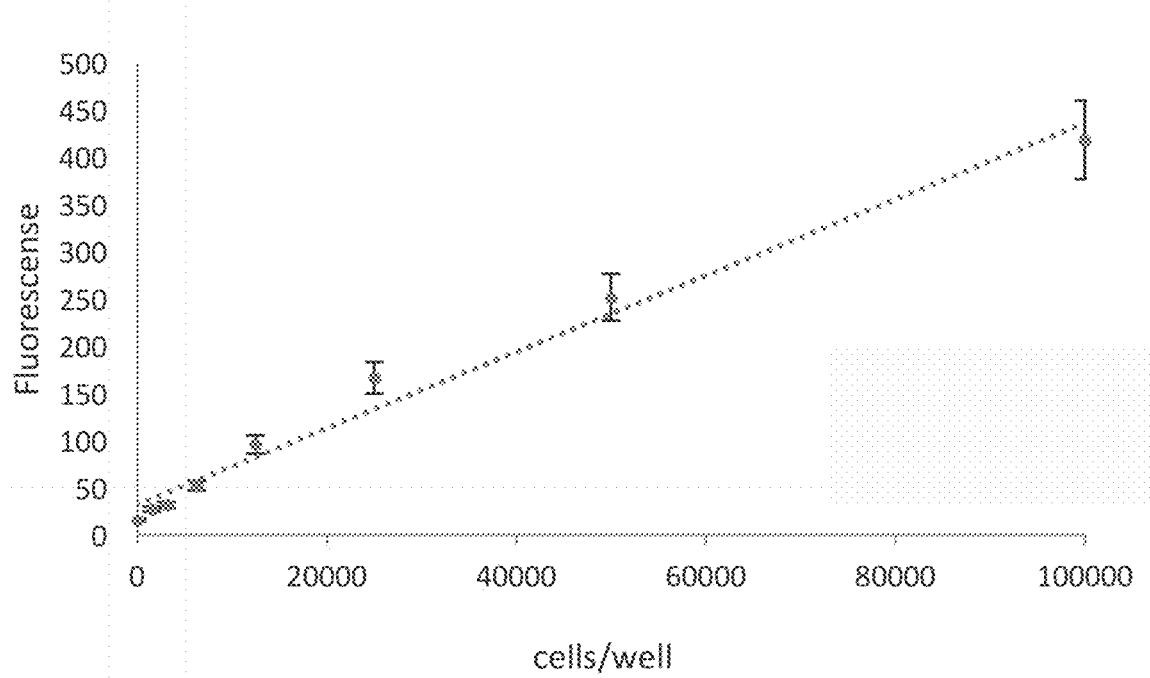
FIG. 7 shows a standard line drawn from the optimization results of alamarBlue® for Hep G2 cells alamarBlue® with excitation at 560 nm and emission at 590 nm.

The measured absorbance was then used to determine the number of viable cells by comparing the measured values to similar samples with known cell amount. A linear standard line was drawn from this data (y=0.004x+32.364, $R^2$=0.98211), shown in FIG. 7.

Results

Morphology of the Cells Remained Unchanged During Freeze-Drying

Figure 8:
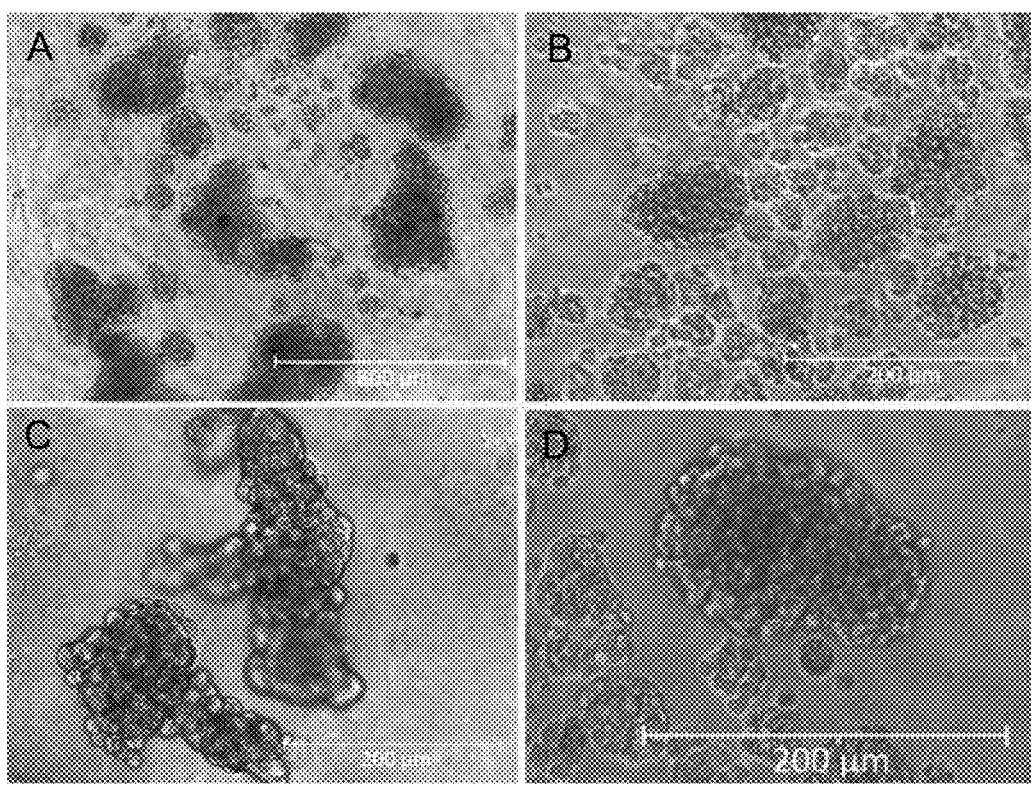
FIG. 8 shows recreated cell hydrogel systems after freeze-drying. (A) extra-large cell spheroids survived the freeze-drying without detachment of cells. (B) different sized cell spheroids after rehydration. (C) Smaller spheroids after rehydration. (D) A cell spheroid with no changes in the morphology after rehydration.

Recreated cell systems were imaged with Leica AF light microscope with ×5 objective (FIG. 8 A), ×10 objective (B) and ×20 objective (C and D). Also, rehydrated systems that were reseeded to cell flasks were imaged with the same microscope. The recreated systems resembled remarkably the original cell cultivations, with no observations of ruptured spheroids. Moreover, the cell morphology appeared to be normal to Hep G2 3D cell cultures. In FIG. 8 (A), extra-large cell spheroids with approximately 300 μm diameter can be observed and in (B), typically sized and shaped spheroids and in (C) red-shaped spheroids. All the different sized spheroids have survived without noticeable rupturing nor collapsing. In (D) the morphology of individual cells can be observed. Also microvesicles on the freeze-dried 3D cell spheroids of HepG2 cells were detected.

SEM Images of the Aerogel

Figure 13:
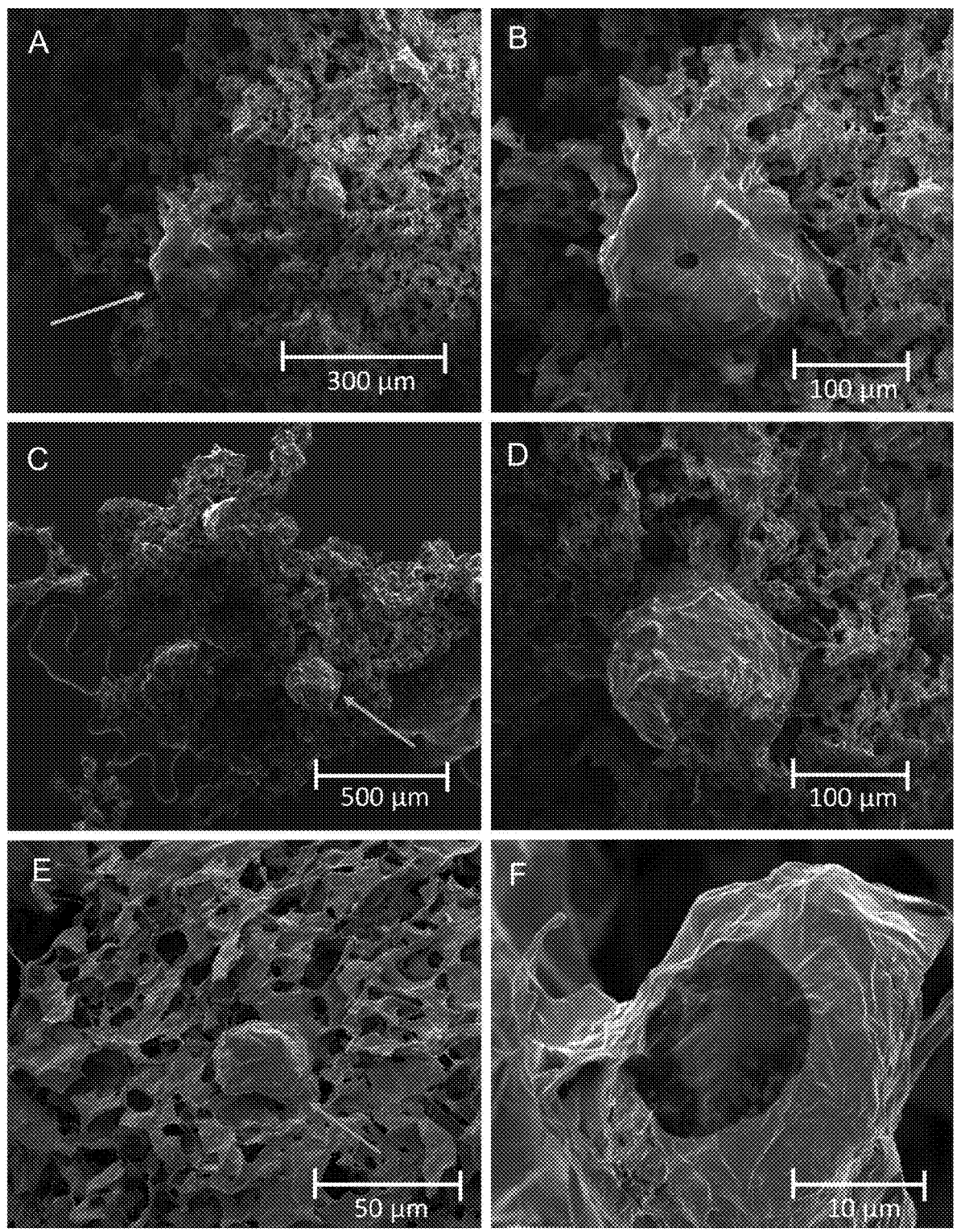
FIG. 13 shows freeze-dried Hep G2 cells and cell spheroids encapsulated in GrowDex® aerogel. (A), (B), (C) and (D) Spheroids of typical size and shape. (E) A tiny cell spheroid. (F) A single Hep G2 cell.

After freeze-drying, the dried samples were imaged with a FEI Quanta™ 250 Field Emission Gun Scanning Electron Microscope (FEG SEM) (FIGS. 13 A-F). The aerogel structure of GrowDex® resembled a typical highly porous cellulose aerogel. Cell spheroids of different sizes could be observed encapsulated in the aerogel (marked with arrows in FIGS. 13 (A), (C) and (E).

Attachment of the Cells

Figure 9:
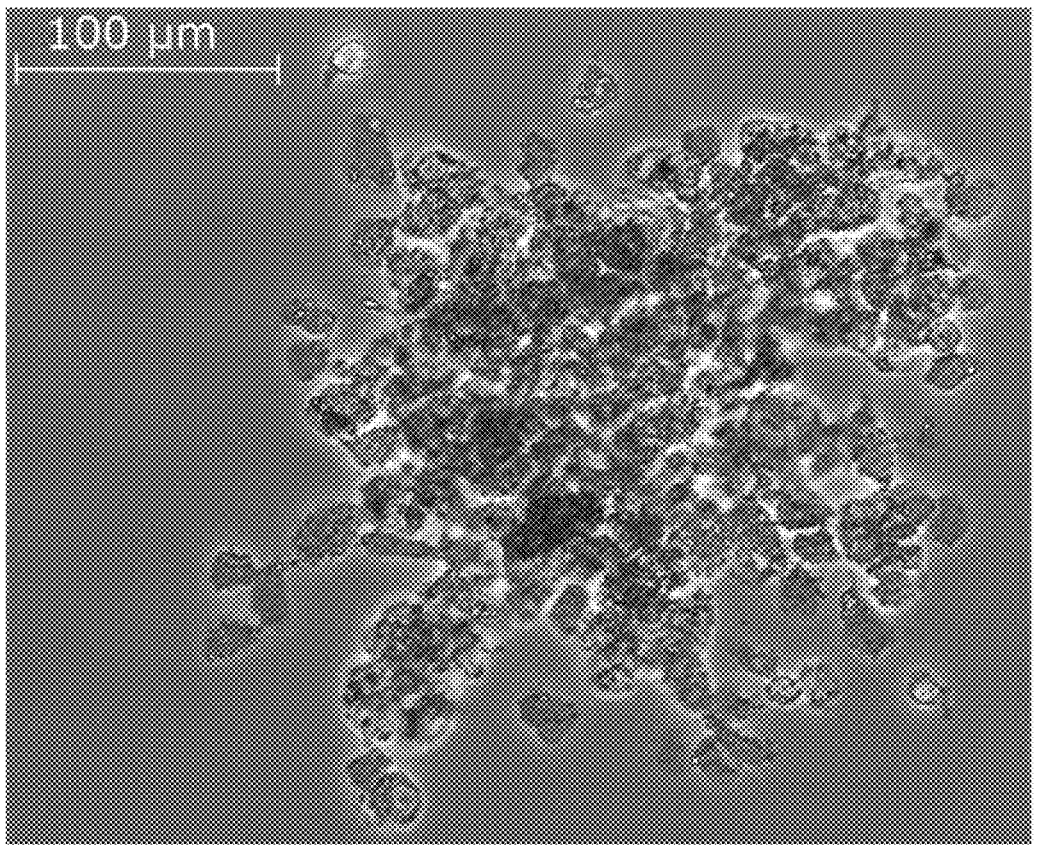
FIG. 9 shows how a 3D cell spheroid has started to attach itself on a 2D surface of a cell culture flask after rehydration and 4 hours after reseeding.

After rehydration, some of the 3D cell spheroids were reseeded to 75 $cm^2$ cell cultivation flasks with fresh medium. After 4 hours, attachment of the cell spheroids on the polypropylene surface of the flask was observed, as presented in FIG. 9. The attachment was strong enough to anchor the spheroid so that it survived the change of medium at the 4-hour point, where the old medium was aspired and new media pipetted to the flask. As the supportive ECM mimicking pressure from the NFC fiber network was gone, morphological changes back to 2D-like structures was observed. However, most spheroids did not attach to the surface during the 4-hour incubation, suggesting lost cell viability.

Cellstain Double Staining Kit for Cell Viability

Cellstain double staining kit (also known as Live/Dead dual staining) by Sigma-Aldrich was used for the determination of cell viability. The amount of active compounds required, calcein AM and propidium iodide, was first optimized in a trial set before the actual measurements. It was determined that 0.2% (v/v) of the provided calcein AM solute and 0.1% (v/v) of propidium iodide solute diluted in 1×DPBS resulted in clear images with 50 000 cells per well with a 15-minute incubation at 37° C. and 5% of $CO_2$.

Figure 10:
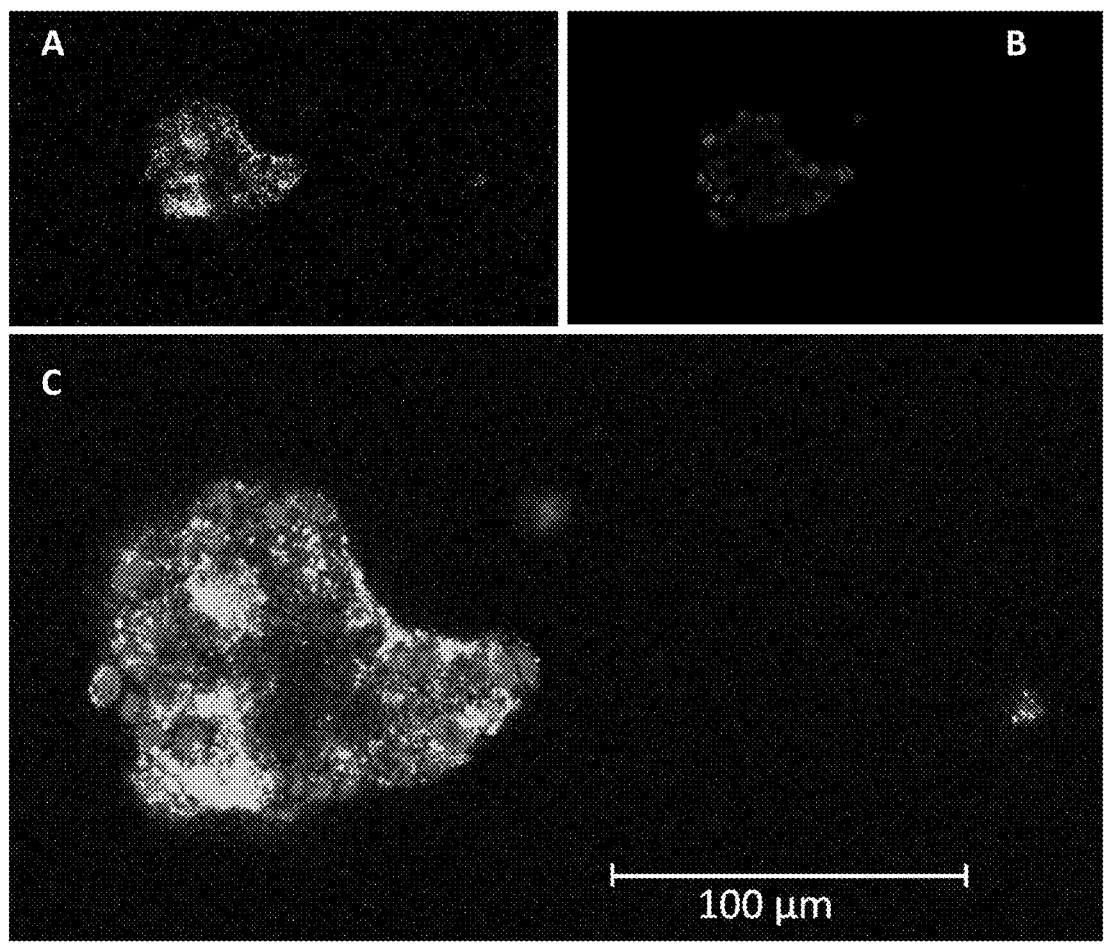
FIG. 10 shows an overlay image (C) of Live/Dead stained cell spheroid after rehydration and double staining containing both viable (A) and dead cells (B).

The rehydrated and dual stained cell samples were imaged with Confocal Microscope Leica SP5 II HCA with the following settings: pinhole 420 μm, gain 480 and argon laser 25%. The used lasers were HeNe 633 nm/12 mW and DPSS 561 nm/20 mW and the used objects were HC PL APO 10×/0.4 (air) and HC PL APO 20×/0.7 CS (air). FIG. 10 shows a cell spheroid 1 hour after rehydration, where (A) shows the channel from the PDSS 561 laser and (B) the channel from HeNe 633 laser. FIG. 10 (C) shows the overlay of these two channels with a higher capture resolution.

Autofluorescence was ruled out by killed control samples that were stained and imaged at the same time showing no green fluorescence in identical settings. The killed control samples were taken from the same rehydrated cell batch, but treated with 70% ethanol for 30 minutes before staining and imagining. Stack images were captured with the confocal microscopy, and 3D models were created in order to analyze the viability rate from the survived cell spheroids. Based on these models, a rate of 25% (±10) cell viability was derived as a result.

Figure 11:
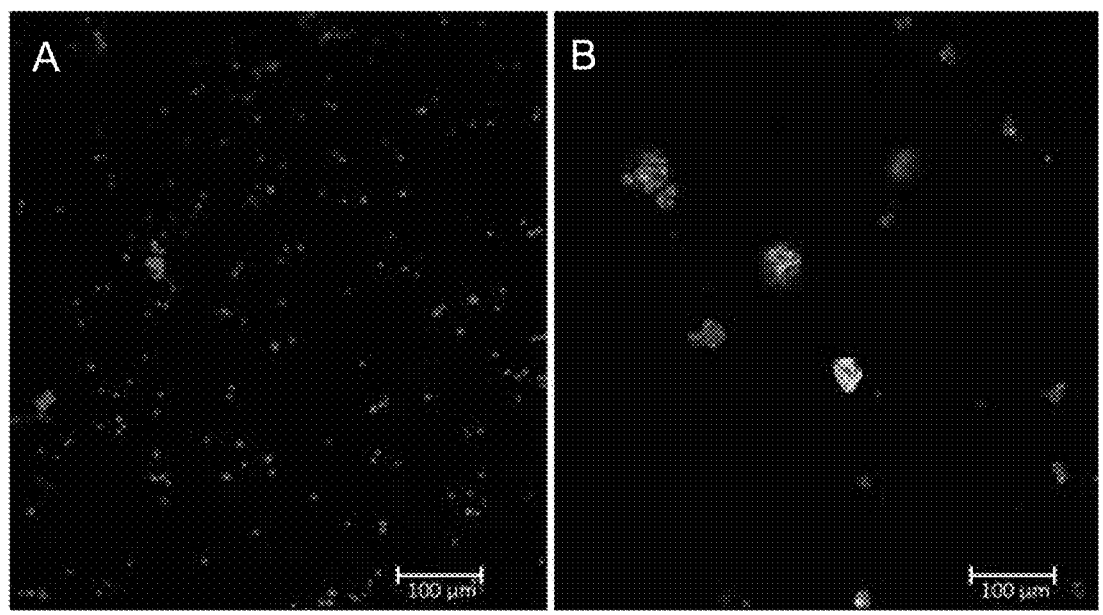
FIG. 11 shows dual stained cells of 2D and 3D cell samples after freeze-drying and rehydration. (A) All cells that did not have the protective effect of GrowDex®, were found dead. (B) Viabilities of 15-35% were estimated in samples with GrowDex®.

Another type of control samples was created to differ the lyoprotective effect of GrowDex®; samples without it, that were otherwise treated the same way including the 24 hour trehalose incubation, same amount of lyoprotectants and freezing with liquid nitrogen. These control samples were freeze-dried with the main samples at the same time to rule out differences between batches. The results are presented in FIG. 11, where all the control samples in (A) were found dead, but live cells were observed in the main samples in (B).

Figure 12:
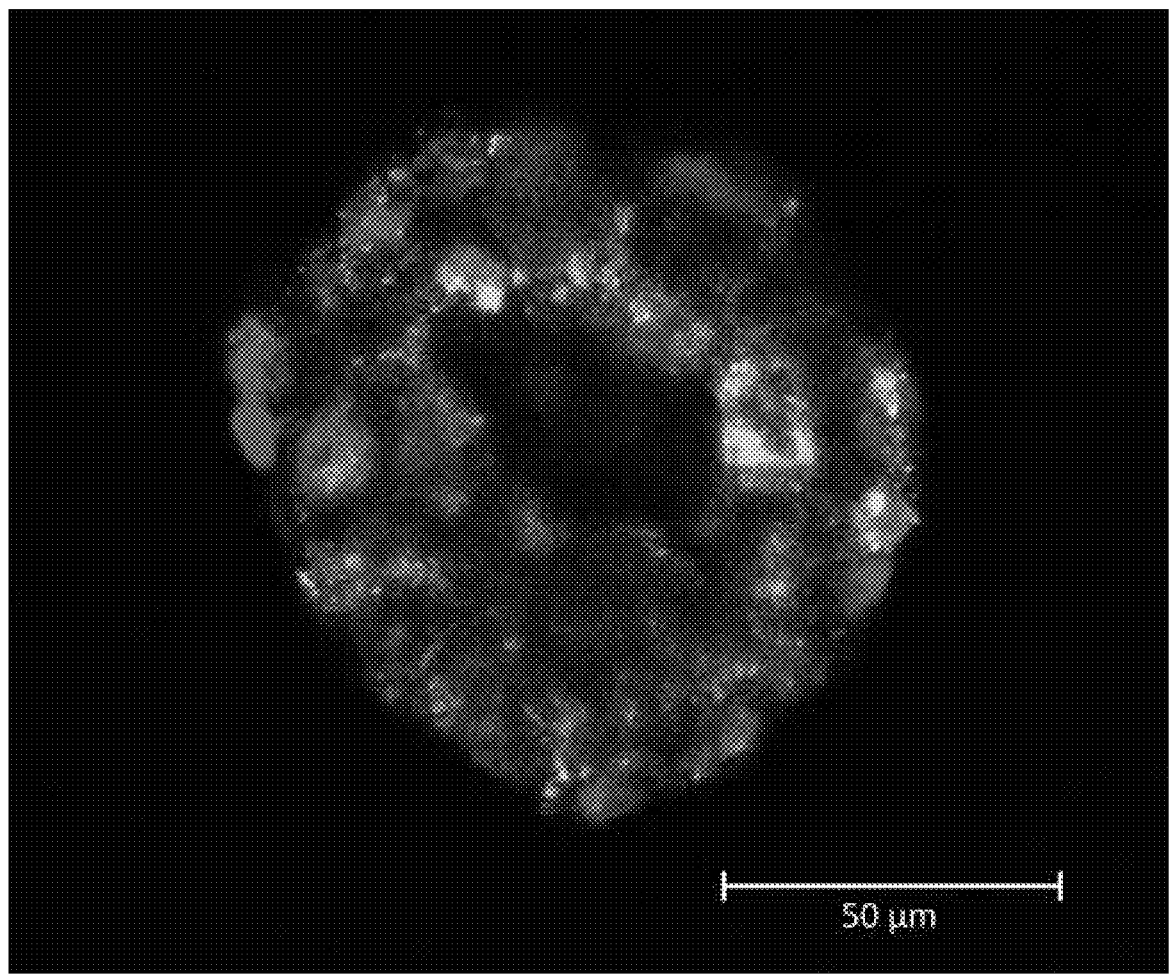
FIG. 12 shows a cell spheroid after rehydration. Dual staining reveals enzyme activity and cells with lost membrane integrity, while some cells have both; partially lost membrane integrity and remaining enzyme activity.

The largest cell spheroids appeared to be hollow in some cases. This might be due to the fact, that the stains were only given 15 minutes time to stain the spheroids and the stains need to diffuse trough the outer cell layers towards the core. This might create an illusion of hollow spheroids, where in reality the stain incubation time should be increased, or the spheroids cut in half before staining. A middle part of a hollow-appearing spheroid is presented in FIG. 12.

With the live/dead images, exact classification to dead an alive is challenging. Some individual cells had both stains, meaning holes in their cell membrane, but enzyme activity inside the cells. Nevertheless, the experiment clearly proves the lyoprotective effects of GrowDex®.

AlamarBlue® Assay

After freeze-drying, the viability of the Hep G2 cells was measured with alamarBlue® assay resulting in 3.7% (±0.03) viability, which is relevantly low. Nevertheless, the viability was detected in several measurement sets, and the alamar-Blue® kit is sensitive enough to detect even 50 viable cells per well. This is still controversy to the results with the Cellstain double staining. One theory was that the freeze-drying changes the properties of GrowDex® and makes it sticky to resazurin. However, this was ruled out by control sample sets, where GrowDex® was first freeze-dried with medium and lyoprotectants but without cells, and healthy cells were seeded after rehydration. Nevertheless, these cells showed normal viability The lack of viability in the alamarBlue® activity measurements proves that something happens to the cell mitochondria during the freeze-drying. Nevertheless, the cell membrane stays intact and cell enzyme proteins stay active as proven by several repeated measurements sets of Cellstain double staining. During the problematic discussion, we referred to the cells as Schrödinger's cells. As both assays were implemented numerous times with always similar results, and all other scenarios were ruled out by comprehensive control measurements, we finally came to the conclusion that the cell membrane remains relevantly intact as no green dye is leaking, while the mitochondria inside the cells are damaged to some extent. One could argue that the NFC prevents the green stain from leaking, but this cannot be the case, as it diffuses from the NFC to the cells in the first place. This dilemma of alamarBlue® is discussed in more detail in the next section.

The nanofibrillar cellulose hydrogels are useful as lyoprotective matrices that can withstand freezing and drying without mechanical rupture, are inert, are clean of contaminants, hold enough liquid to achieve high porosity and can be shaped as well-defined geometrical units. According to the tests, the nanofibrillar cellulose produced by UPM-Kymmene Oyj fulfils all of these requirements. The NFC matrix did release the absorbed active product when flooded with the rehydration liquid. If a correct amount of cellulase enzyme mixture (GrowDase™) is added, the nanofibrillar cellulose fiber structure is digested to small sugars. However, in the case of freeze-dried 3D cell spheroid hydrogel systems, the cultivation is most likely continued in the hydrogel environment, and therefore there is usually no need to digest the hydrogel in the first place.

As to the requirements for freeze-dried products that the dried product should be dry, active, shelf stable, clean and sterile, ethically acceptable, pharmaceutically elegant, readily soluble and simple to reconstitute and the process should be economically practicable, also these requirements were met. Based on the findings, the dried GrowDex® Hep G2 system had no free water left in it, retained its activity after reconstitution, was sterile, elegant and readily soluble. As the GrowDex® and all other components are completely animal free, the process should be considered ethically acceptable, as long as the used cells have no ethical issues. If the required machinery is available, all materials used in the process are relevantly inexpensive (sugars, cellulose, glycerol), yet the final product can be of high value. If the process is further optimized in factory settings, it can be considered as economically practicable. The shelf stableness of the product was not researched beyond days due to tight schedule. Also, the freeze-dried samples were transferred in dry state encapsulated in NFC from West-Finland to Helsinki in a car trunk on a highway—yet the samples still showed viability. It could be due to the rigid dry structure of the NFC fibers that prevent the hollow cells from collapsing.

The invention claimed is:

1. A method for freeze-drying extracellular vesicles in a hydrogel comprising nanofibrillar cellulose, the method comprising:
   providing a hydrogel comprising nanofibrillar cellulose,
   providing extracellular vesicles,
   combining the extracellular vesicles and the hydrogel comprising nanofibrillar cellulose to form a vesicle system, and
   freeze drying the vesicle system to obtain freeze-dried extracellular vesicles in an aerogel comprising freeze-dried nanofibrillar cellulose;
   wherein the nanofibrillar cellulose is selected from anionically modified nanofibrillar cellulose, cationically modified nanofibrillar cellulose and unmodified nanofibrillar cellulose, and TEMPO oxidized nanofibrillar cellulose.

2. The method of claim 1, wherein the extracellular vesicles comprise exosomes or microvesicles.

3. The method of claim 1, further comprising providing one or more cryoprotective agent(s) and/or one or more lyoprotective agent(s), and adding the one or more cryoprotective agent(s) and/or one or more lyoprotective agent(s) to the vesicle system.

4. The method of claim 3, wherein the one or more cryoprotective and/or lyoprotective agent(s) is selected from trehalose, glycerol, and polyethylene glycol.

5. The method of claim 3, wherein the one or more cryoprotective and/or lyoprotective agent(s) comprise trehalose and glycerol.

6. The method of claim 1, wherein the nanofibrillar cellulose has a number average fibril diameter of 1 to 100 nanometers.

7. The method of claim 1, wherein the nanofibrillar cellulose, when dispersed in water, provides a zero-shear viscosity of 5000-50000 Pa·s and a yield stress of 3-15 Pa, determined by rotational rheometer at a consistency of 0.5% (w/w) in aqueous medium at 22° C.

8. The method of claim 1, wherein the concentration of the nanofibrillar cellulose in the hydrogel before the freeze-drying is in the range of 0.1-10% (w/w).

9. The method of claim 1, wherein the freeze drying is continued until the dried hydrogel has a moisture content of 10% (w/w) or less.

10. A freeze-dried aerogel comprising freeze-dried nanofibrillar cellulose and freeze-dried extracellular vesicles, wherein the moisture content of the hydrogel is 10% (w/w) or less wherein the nanofibrillar cellulose is selected from anionically modified nanofibrillar cellulose, cationically modified nanofibrillar cellulose and unmodified nanofibrillar cellulose, and TEMPO oxidized nanofibrillar cellulose.

11. The freeze-dried aerogel of claim 10, wherein the extracellular vesicles comprise exosomes or microvesicles.

12. The freeze-dried aerogel of claim 10, further comprising one or more cryoprotective agent(s) and/or one or more lyoprotective agent(s).

13. The freeze-dried aerogel of claim 12, wherein the one or more cryoprotective and/or lyoprotective agent(s) is selected from trehalose, glycerol, and polyethylene glycol.

14. The freeze-dried aerogel of claim 12, wherein the one or more cryoprotective and/or lyoprotective agent(s) agents comprise trehalose and glycerol.

15. The freeze-dried aerogel of claim 10, wherein the content of the extracellular vesicles in the freeze-dried aerogel is in the range of 0.1-65% (w/w).

16. The freeze-dried aerogel of claim 13, wherein the content of the one or more cryoprotective and/or lyoprotective agent(s) is in the range of 1-10% (w/w) and/or the content of the trehalose is in the range of 0.5-50% (w/w) in the freeze-dried aerogel.

17. The freeze-dried aerogel of claim 10, wherein the nanofibrillar cellulose has a number average fibril diameter of 1 to 100 nanometers.

18. The freeze-dried aerogel of claim 10, wherein the nanofibrillar cellulose, when dispersed in water, provides a zero-shear viscosity of 5000-50000 Pa·s and a yield stress of 3-15 Pa, determined by rotational rheometer at a consistency of 0.5% (w/w) in aqueous medium at 22° C.

19. The freeze-dried aerogel of claim 10, obtained with the method of the claim 1.

* * * * *